United States Patent
Kulmala et al.

(10) Patent No.: US 6,645,776 B2
(45) Date of Patent: *Nov. 11, 2003

(54) ELECTRICAL EXCITATION OF LABEL SUBSTANCES AT INSULATING FILM-COATED CONDUCTORS

(75) Inventors: Sakari Kulmala, Kirkkonummi (FI); Timo Ala-Kleme, Mellilä (FI); Jarkko Eskola, Turku (FI); Timo Korpela, Turku (FI)

(73) Assignee: Labmaster Oy, Turku (FI)

( * ) Notice: Subject to any disclaimer, the term of this patent is extended or adjusted under 35 U.S.C. 154(b) by 0 days.

This patent is subject to a terminal disclaimer.

(21) Appl. No.: 09/779,881

(22) Filed: Feb. 9, 2001

(65) Prior Publication Data

US 2002/0081749 A1 Jun. 27, 2002

Related U.S. Application Data

(63) Continuation of application No. 09/341,955, filed as application No. PCT/FI98/00114 on Feb. 10, 1998, now Pat. No. 6,251,690.

(30) Foreign Application Priority Data

Feb. 12, 1997 (FI) .................................... 970593

(51) Int. Cl.[7] ............................................ G01N 33/543
(52) U.S. Cl. ................................ 436/518; 435/5; 435/6; 435/7.1; 435/7.2; 435/7.4; 435/968; 436/525; 436/172; 436/805; 436/806; 436/816; 422/82.08; 204/400; 204/403
(58) Field of Search ...................... 435/5, 6, 7.1, 7.2, 435/7.4, 968; 436/518, 525, 172, 805, 806, 816; 422/82.08; 204/400, 403

(56) References Cited

U.S. PATENT DOCUMENTS

| | | | |
|---|---|---|---|
| 4,280,815 A | 7/1981 | Oberhardt et al. | |
| 4,835,059 A | 5/1989 | Kodato | |
| 5,262,299 A | 11/1993 | Evangelista et al. | |
| 5,308,754 A | 5/1994 | Kankare et al. | |
| 5,340,714 A | 8/1994 | Katsilometes | |
| 5,591,581 A | 1/1997 | Massey et al. | |
| 5,624,711 A | 4/1997 | Sundberg et al. | |
| 5,714,274 A | 2/1998 | Sugiura et al. | |
| 5,716,781 A | 2/1998 | Massey et al. | |
| 6,251,690 B1 * | 6/2001 | Kulmala et al. ............ 436/518 | |

FOREIGN PATENT DOCUMENTS

GB        2217007 A        10/1989

OTHER PUBLICATIONS

Kankare et al. (1992). Immunoassay by time–resolved electrogenerated luminescence. Analytica Chimica Acta. 266:205–212.

(List continued on next page.)

Primary Examiner—Christopher L. Chin
Assistant Examiner—Gailene R. Gabel
(74) Attorney, Agent, or Firm—James C. Lydon

(57) ABSTRACT

The excitation of label molecules usable in chemical and biochemical analysis by electrical pulses at electrodes covered with a thin insulating film, and the use of such electrodes in chemical, clinical and biochemical analysis. The electrodes include a conducting base material that has been coated with an organic or inorganic insulating film or multiple layers of such films, so that either one or several label compounds can be excited to an excited state which is deexcited by emission of ultraviolet, visible or infrared light, in aqueous solution providing the basis for reproducible analytical applications in bioaffinity assays such as immunoassays and DNA-probing assays.

28 Claims, 10 Drawing Sheets

OTHER PUBLICATIONS

Kulmala et al. (1991). Electrogenerated luminescence of terbium(III) in aqueous solutions. Analytica Chimica Acta. 252:65–76.

Kankare et al. (1992). Cathodically induced time–resolved lanthanide(III) electroluminescence at stationary aluminum disc electrodes. Analytica Chimica Acta 256:17–28.

Alwitt et al., "Voids in Anodic Aluminum Film," 129 J. Electrochem. Soc., 711–17 (1982).

Thompson et al., "Observations of Flaws on Preconditioned Aluminum Surfaces," 129 J. Electrochem. Soc., 1515–1516 (1982).

Shimizu et al., "Direct Observation of Voids and Cracks in the Barrier Oxide Layer of Composite Aluminum Oxide Films," 132 J. Electrochem. 1384–85 (1985).

Y. Ono, "Electroluminescent Displays" page 9 (May, 1995).

S. Morrison, "Flatband Potentials for Various Semiconductors" table 5.4, page 186, (1990).

* cited by examiner

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:
      oligonucleotide containing amino groups

<400> SEQUENCE: 1
agatgctact ggccgctgaa gggctt                                    26

<210> SEQ ID NO 2
<211> LENGTH: 28
<212> TYPE: DNA
<213> ORGANISM: Artificial Sequence
<220> FEATURE:

-continued

<223> OTHER INFORMATION: Description of Artificial Sequence:
      oligonucleotide containing an amino group

<400> SEQUENCE: 2
ttccttattg atggtcagcg gaatgctg                                              28

ELECTRICAL EXCITATION OF LABEL SUBSTANCES AT INSULATING FILM-COATED CONDUCTORS

This application is a continuation of application Ser. No. 09/341,955, filed Jul. 21, 1999 and now U.S. Pat. No. 6,251,690, which is the National Stage of PCT/FI98/00114, filed Feb. 10, 1998 and published in the English language on Aug. 20, 1998.

FIELD OF INVENTION

The present invention relates to electrical excitation of label substances at electrodes covered with insulating layer/layers and utilisation of the resulting luminescence (electogenerated luminescence, EL) in analytical methods, especially in bioaffinity assays.

BACKGROUND OF INVENTION

Many commercially important analytical methods are bused on the principle that the analytes can be recognised and quantified from a matrix using label substances. For instance, in the assays based on the biological properties of analytes, such as in immunoassays, the analyte (A) can be selectively captured from a solution upon a solid support with the aid of antibodies immobilised on the surface of the solid support, and the amount of (A) can be quantified using another antibody selectively binding with (A) and being labelled with a suitable marker substance. Such a marker substance can be, for instance, radioactive isotope, enzyme, molecule that absorbs light or produces fluorescence or phosphorescence, certain metal chelates etc., which can be coupled with chemical bonds with an antibody. Alternatively, purified (A) can be labelled (A–L) and the amount of unlabelled (A) can be determined by antibodies immobilised on a solid support with by exploiting competitive reactions between (A–L) and analyte (A). DNA- and RNA-probing assays are based on the analogous bioaffinity principles as immunoassays and can be performed along with related procedures. Also, other chemical and biochemical analysis methods can be based on analogous principles. Presently, there is an increasing need for multiparameter assays due to a growing demand to decease the costs and/or increase the simplicity and accuracy of determinations. One solution to these problems is the use of label compounds luminescing at different wavelengths. Various methods and strategies in immunoassays are described, e.g., in "The Immunoassay Handbook". Edited by David Wild. Stockton Press Ltd., New York, 1994, pages 1–618.

It is already known that organic luminophores and metal chelates suitable for labelling in analytical methods can be excited with light or by electrochemical means resulting in the specific emission from the labelling substance. The methods based on these phenomena are generally sensitive and well-suited for the excitation of label substances. However, difficulties are encountered when the concentrations of labels in real assays are very low; e.g., the use of fluorescence is complicated by the existence of Tyndall, Raleigh, and Raman scattering, and by the background fluorescence common in biological samples. Phosphorescence in liquid phase is mainly usable only in connection with some specially synthesised lanthanide chelates. Utilisation of the long-lived photoluminescence of these compounds is restricted mainly due to complicated apparatus required and high cost of pulsed light sources.

Electrochemiluminescence can be generated in non-aqueous solvents at inert metal electrodes with a rather simple apparatus. However, bioaffinity assays which are of commercial importance are normally applicable in aqueous solutions only. Samples are practically always aqueous and therefore the demon method of a label substance must be applicable in aqueous solution. Presently, only certain transition metal chelates can serve as electrochemiluminescent labels in micellar solutions, which in principle, are not fully aqueous solutions. However, these methods utilising conventional electrochemistry and inert metal electrodes do not allow simultaneous excitation of several label substances possessing sufficiently differing emission spectra and/or luminescence lifetime.

Mainly inert active metal (e.g. Pt and Au) or carbon electrodes are applied in conventional electrochemistry. Their utilisation is restricted to a narrow potential window due to the water decomposition reactions, hydrogen and oxygen evolution. Luminophores usable as fluoresent or phosphorescent labels cannot normally be electrically excited in aqueous solution at these electrodes due to the inaccessibility of the highly anodic and cathodic potentials required for the excitation reactions. With suitably selected semiconductor electrodes a wider potential window is achievable, but only very rare labelling substances can be excited at this type of electrodes in filly aqueous solutions.

The present invention provides considerable improvement for use of active metal electrodes or semiconductor electrodes and makes it possible to simultaneously excite a variety of different labelling substances in fully aqueous solution. The invention utilises a new type of electrodes, conductors covered with an insulating film, which are useless in the field of conventional electrochemistry. Below these electrodes are called either insulator electrodes or insulating film-coated electrodes.

SUMMARY OF THE INVENTION

This invention relates to the excitation of label molecules useable in chemical and biochemical analysis by electrical pulses at electrodes covered with a thin insulating film, and the use of such electrodes in chemical, clinical and biochemical analysis. The electrodes consist of a conducting base material that has been coated with an organic or inorganic insulating film or multiple layers of such films, so that either one or several label compounds can be excited to an excited state which is deexcited by emission of ultraviolet, visible or infrared light, in aqueous solution, thereby providing the basis for reproducible analytical applications in bioaffinity assays such as immunoassay and DNA-probing assays.

DETAILED DESCRIPTION OF THE INVENTION

Figure 1:
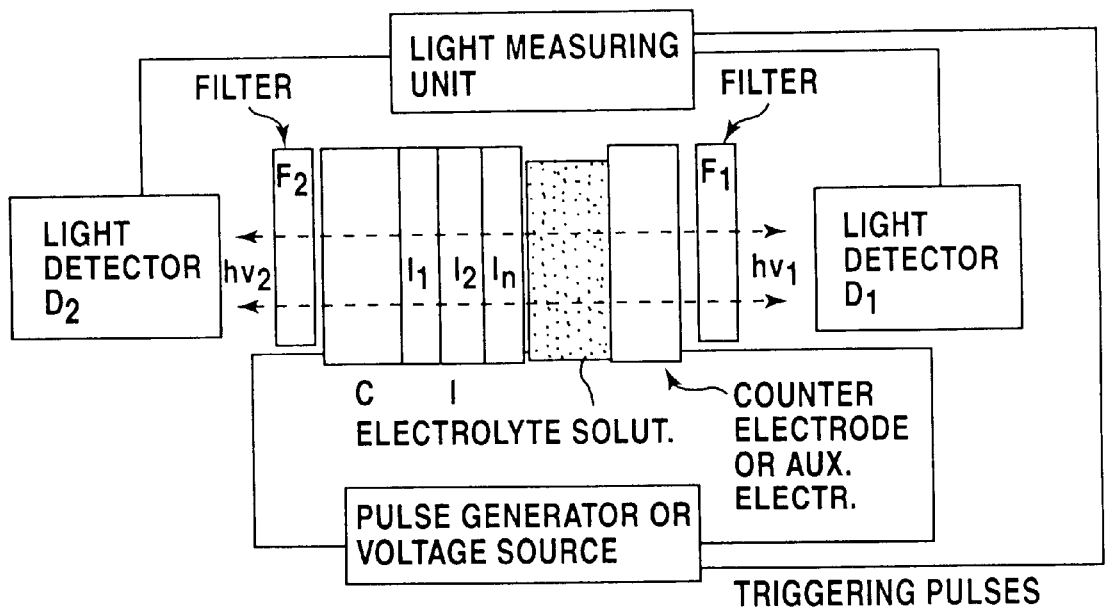
FIG. 1 illustrates a measurement apparatus which incorporates the insulating film-coated electrodes used in the method of the present invention.

The aim of the invention is a method and apparatus, with which one or several different types of label substances can be simultaneously electrically excited, so that the resulting luminescence can be utilised in bioaffinity assays such as immunoassays and DNA or RNA probing assays.

It has been experimentally observed that extremely harsh redox conditions can be produced at aluminium electrodes, and that these conditions closely resemble those of radiolysis of water (S. Kulmala, "Electrogenerated lanthnide(III) luminescence at oxide-covered aluminium electrodes and closely related studies", Academic dissertation, Turun yliopisto, 1995). Electrically induced luminescence at aluminium electrodes has already been studied for several years using irreproducible results-yielding electrodes with natural oxide film coverage as described e.g. in references: J. Kankare, K. Fälden, S. Kulmala and K. Huaapakka, *Anal. Chim Acta,* 256 (1992) 17. and J. Kankare, K. Haapakaa, S. Kulmala, V. Nänto, Eskola and H. Takalo, *Anal. Chim. Acta,* 266 (1992) 205. The nature of the metal itself was assumed to be the most important component of the system and the importance of the naturally existing 1–2 nm thick oxide film was not understood. For instance, in the life, tantalum Electrodes were claimed to be fully equivalent with album electrodes and usable in the same applications as aluminium electrodes (UK Patent GB 2 217 007 B). However, tantalum oxide is an n-type semiconductor with a band gap ca. 4 eV (S. Morrison, "Electrochemistry at Semiconductor and Oxidised Metal Electrodes", Plenum Press, New York, 1980, s.183) and, therefore, oxide covered tantalum electrodes cannot be used according to the principles of the present invention. In the present invention, insulator electrode is defined as an electrode on which at least one of the coating layers consists of material that has band gap larger than or equal to 5 eV.

The present invention is based on a thin, normally close to 4 nm thick, good-quality insulating film, upon the surface of which or in the vicinity of which the bioaffinity reactions are performed, or to the vicinity of which the products of the bioaffinity reaction are brought with a suitable medium such as electrolyte solution, or upon suitable supporting material such as surface of magnetic latex particles. The applicability of the present invention is partially based on the fact that the existence of an insulating film enables the Fermi-level of the base conductor to reach highly cathodic pulse potentials, and subsequently allows a transfer of energetic (hot) electrons into the electrolyte solution, either by tunnelling through the insulating film or as a consequence of an electron avalanche, If the Fermi level of the electron-emitting base conductor is above the conduction band edge of water (−1.3 eV on vacuum scale), the hot electrons can be injected into the conduction band of water and thus produce hydrated electrons as cathodic mediators for reduction reactions as has been described in the cases of radiolysis of water or photoionisation of solutes.

The insulating film on the electrodes also provides the basis for the Fermi level of the base conductor to reach highly anodic pulse potentials, which makes a new anodic process, a hole injection into the valence band of water, possible. This process is analogous to the electron injection into the conduction band of water, and results in the generation of hydroxyl radicals by dissociation of $H_2O^+$-ion formed (valence band hole in the water) to proton and hydroxyl radical as known from the pulse radiolysis of water. Certain metal oxides, $Al_2O_3$, $SiO_2$, and MgO, may produce hydroxyl radical also by other solid state mechanisms as described in references: S. Kulmala, T. Ala-Kleme, A. Kulmala, D. Papkovsky and K. Loikas, "Cathodic Electrogenerated Chemiluminescence of Luminol at Disposable Oxide-covered Aluminum Electrodes", Anal. Chem., in press.; S. Kumala & T. Ala-Kleme, Anal. Chim. Acta, 355 (1997) 1–5.

Hydroxyl radical, having a strong tendency to addition and hydrogen abstraction reactions, can be transformed into other oxidising radicals which are better suited reactants in producing redox luminescence. These secondary oxidising radicals can be produced by addition of anions from the halide, and pseudo-halide series into the measuring electrolyte solution ($X^-$=halide or pseudo-halide-ion);

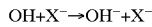
$$OH + X^- \rightarrow OH^- + X$$

If an insulating film is incapable of producing hydroxyl radicals by the above-mentioned mechanisms or if one wishes to increase the amount of oxidising species at the expense of reducing equivalents, hydroxyl radicals can be generated from hydrogen peroxide according to reaction:

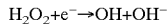
$$H_2O_2 + e^- \rightarrow OH + OH^-$$

An analogous technique also allows the production of sulfate and phosphate radicals, which are often better suited oxidants for the redox excitation pathways than hydroxyl radicals (S. Kulmala T. Ala-Kleme, A. Kulmala, D. Papkovsky and K. Loikas, "Cathodic Electogenerated Chemiluminescence of Luminol at Disposable Oxide-covered Aluminum Electrodes", Anal. Chem, in press.):

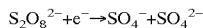
$$S_2O_8^{2-} + e^- \rightarrow SO_4^- + SO_4^{2-}$$

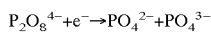
$$P_2O_8^{4-} + e^- \rightarrow PO_4^{2-} + PO_4^{3-}$$

The protonation of phosphate radicals affect the oxidising power of the radical whereas the oxidising power of sulfate radical is independent of the pH above pH 2.

Hence, highly oxidising and reducing conditions can be created simultaneously in the vicinity of insulating film-coated electrodes, which is usually a prerequisite for the existence of redox luminescence in aqueous solution.

Although the solid state phenomena utilised in this invention are known in the theories of physics, the present type of insulator electrodes has not been utilised in analytical chemistry, except in the case of album electrodes covered with naturally existing poor-quality and too thin oxide film (UK Patent GB 2 217 007 B) that have not led to any practical applications of such aluminium electrodes. On the contrary, the present invention forms a major improvement of the said electrodes by realising the correct role of the insulating films and their deliberate preparation.

According to the present invention, electrodes have a conductive base layer that can be composed of e.g., carbon (graphite, glassy carbon) or metal such as Be, Mg, Al, Ga, In, Au Pt, Cu, Fe, Ru, stainless steel, Zn, Hg, Ag, Ni, Pd, Hf, Zr, (also Ta is suitable as the base conductor although $Ta_2O_5$ is not usable as an insulating film). However, it is possible that the electrode works better the smaller the work function of the base conductor is.

The conductor can be also a heavily doped semiconductor or metal oxide such as Si, Ge, Sr, ZnO, $SnO_2$ etc. The base conductor can be also composed of conductive polymer such as polyaniline, polypyrrole, polyacetylene, polytiophene or of corresponding polymers made from substituted monomers. The resistivity of the base conductor should be <10 Ωcm.

Insulating layer(s) of the electrode can be made of some metal oxides, such as, $SiO_2$, MgO, CaO, SrO, BaO, $Al_2O_3$, $HfO_2$; of some other inorganic insulators, such as diamond, silicates or nitrides, some organic insulating materials such as paraffines, other solid or liquid hydrocarbons, organic insulating polymers such as, Teflon, polyethene, polypropene, polystyrene, polyacrylamides, epoxy-plastics etc. Normally metal oxides can be used as insulating film material only in the case of utilisation of pulsed excitation, because DC-cathodisation normally ruins the insulating properties of the oxide films within few milliseconds.

Coating film of the electrodes can be manufactured by anodic oxidation, by Atomic Layer Epitaxy (ALE), by spraying polymeric or polymerisable material on the surface of the electrode, by dipping the electrodes in the above-mentioned solution and letting the solvent evaporate, by Langmuir-Blodgett methods or by other methods known from other coating processes. Especially in the case of silicon, there are several alternative methods to manufacture good-quality $SiO_2$ films known in the electronics industry.

Although, in principle, naturally existing oxide film-covered aluminum electrodes can be used to excite some label substances, the commercial utilisation of these electrodes is impossible due to the poor quality of the natural oxide film which results in the too high irreproducibility of the analysis results (S. Kulmala, "Electrogenerated lanthanide(III) luminescence at oxide-covered aluminium electrodes and closely related studies", Academic dissertation, Turun yliopisto, 1995, pp. 25–31 and 114–119.) However, the reproducibility of the analysis can be improved to the level required, by fabrication of good-quality insulating film with suitable thickness. It is characteristic for the present invention that the coating film/films are carefully layered upon the base conductor taking care that the total thickness of coating is opt . In the case of aluminium, this kind of insulating film cannot be produced by letting aluminium to be oxidised in air, but can be manufactured by other methods. A preferred method is anodic oxidation of aluminium in suitable electrolyte solution and successive coating with organic material(s) to prevent the aqueous solution spoiling the insulating properties of the oxide film during the bioaffinity assays that is always inevitable to some degree in the absence of other shielding coating layers. Aluminium oxide film can also be made by coating some other material with aluminium, such as plastic, graphite, glassy carbon, metal, and subsequently oxidising aluminium and adding a final shielding layer.

When an aluminium oxide film is immersed in an aqueous solution, depending on the solution conditions, various uncontrollable processes start to proceed in the oxide film commencing from the outer part of the layer. Consequently, the properties of the naturally existing very thin (1–2 nm thick) spontaneously formed oxide film change as a function of time and induce strong decrease in the EL generation efficiency, As pointed out in Example 1, in aqueous solution the EL generation efficiency decreases 90% dung coating with a protein film necessary as the first step of any immunoassay. This drawback can be prevented, when the oxide film has been fabricated to optimal thickness and preferably covered with an additional shielding thin film, such as an organic insulating polymer film. Some organic polymers are also especially beneficial because they improve the coatability of the electrodes with antibodies and other biomaterials.

In bioanalytical methods, DNA- and RNA-probing techniques are practically as important techniques as immunoassays. Aluminium electrodes covered with thin naturally existing oxide film arc unexpectedly not at all applicable in nucleic acid hybridisation assays. However, it was experimentally found out that even aluminium. eletrodes become useful also in these methods, if the oxide film is coated with a thin organic film such as polystyrene layer.

Suitable polymeric films can be readily created by dipping the electrode in polystyrene solution which has been made by dissolving polystyrene in an organic solvent such as benzene or toluene. In an analogous way, also many other polymers that can be dissolved as dilute solutions of solvents can be utilised in fabrication of thin polymer films. Among usable polymers there can be mentioned: polyamides, polyamines, polybutadienes, polycarbonates, polyenes, polyesters, polyethylenes, polyethyleneimides, polyformaldehyde etc. as has been described in the textbooks of polymer chemistry. Polymeric films can also be made from mixtures of polymers or they can be doped with inorganic materials. Polymeric film can be made exceptionally smooth by using commercially available apparatuses for growing of these films. The electrode surface need not to be totally coated with an insulating film designed for active use in excitation of labels, but insulating films can be in the form of very small spots or islands, surrounded by a thicker insulating film not allowing current transport with any mechanism. The electrodes are not necessarily always platelike, but can also have a shape of a net, spike(s), tube(s), a plate with hole(s), etc.

Analogous polymeric films can be created also by allowing polymerisation to occur at the surface of a conductor or at the surface of insulating film-covered conductor. In this case, the reactants of polymerisation reaction ate dissolved separately in a suitable inert solvent such as toluene, benzene, dichlormethane, etc. One of the components can be deposited with a special deposition device, or the electrode is automatically dipped in a solution of the component and solvent is allowed to evaporate. Another component can be deposited in an analogous way and polymerisation is allowed to occur. Alternatively, the reactants of polymerisation reaction are mixed in a solvent just before deposition. In all cases, the optimal thickness of the films can be experimentally found by adjusting the concentration of coating materials in the solvents or by using coating apparatus for adjustment of the film thickness. In some cases it is preferable to coat electrodes by spraying. Polymer must be divided in the spray to droplets with diameter 1–1000 nm in an appropriate solvent, such as, toluene, benzene, cyclohexane, chlorinated hydrocarbons, DMF, DMSO, or alcohols.

The main drawback of aluminium oxide films is that they cannot tolerate either basic or acidic conditions. This drawback can be prevented by an extra shielding layer or replacing aluminium oxide films with other insulating films. MgO films are suitable especially in basic conditions because these films are not dissolved in basic aqueous solutions. MgO films can be made e.g. by ALE-techniques and also these films can be coated with other films as pointed out above in the case of aluminium oxide films.

$Al_2O_3$, MgO and other alkaline earth metal oxide coatings are less studied than rather well known $SiO_2$ films. $SiO_2$ is the most important insulating film material in electronics industry based on silicon technologies. There are several methods available for fabrication of good-quality $SiO_2$ films in this field of industry. Therefore, technically mature silicon technology is preferable in the fabrication of the electrode materials utilised in the embodiment of this invention.

Inorganic insulating films can be totally replaced with suitable organic insulating films, if the production of oxidising species, generally necessary for excitation most of the label substances, is provided by addition of suitable coreactants such as peroxydisulfate, peroxydiphosphate, or hydrogen peroxide which produce strongly oxidising radicals via one-electron reduction. Often, the combination of inorganic and organic film is preferable.

The present invention makes a dramatic improvement over the prior art specially, with increasing the reproducibility to a level required in practical analytical methods. Other advantages of the present invention are the excitation event itself and the accurate timing of excitation. In addition, a number of very differing label substances (emission spectra and luminescence lifetimes of which are different) can be simultaneously excited which allows multiparametric assays Example 17). They also render a possibility to improve accuracy of determinations by internal standardisation. For instance, in homogeneous assays where unreacted excess label is not separated from immunocomplexes, dual labelling enables to quantitate simultaneously two different antibodies or their concentration ratio (Example 23). This allows efficient exclusion of matrix effects arising from deviating sample compositions often preventing the exploitation of homogeneous assays. Other major advantages of the present invention is the simplicity and low cost of the measuring instrument.

According to the present invention many types of luminophores can serve as the labels. For instance, the following luminophores (or derivatives of them) can be utilised: 9-fuorenylmethylchloroformate (emission 309 nm), luminol (emission 420 mn), fluorescein (emission 516 nm), salicylates (emission in the region 400–450 nm), aminonaphthalene sulphonates (emission in the range of 400–500 nm) and coumarines (emission in the range of 450 nm–550 nm), aromatic lanthanide(III) chelates, such as certain derivatives of terbium(III) complexes with following ligands: $N^1$-(4-aminobenzyl)diethylenetriamine-$N^1,N^2,N^3,N^3$-tetra-acetate (Tb(III)-1), 4-(phenyl-ethyl)(1-hydroxybenzene)-2,6-diyl) bis-methylenenitrilo)tetrakis(acetate) (Tb(III)-2); 4-benzoyl (1-hydroxybenzene)-2,6-diyl)-bis(methylenenitrilo)tetrakis(acetate) (Tb(III)-3), $N^2$-(4-aminobenzyl)-diethylenetriamine-$N^1,N^1,N^3,N^3$,-tetra-acetate (Tb(III)4); 4-methyl(1-hydroxybenzene)-2,6-diyyli)bis(methylenentrilo)tetakis(acetate) (Tb(III)-5)(The strongest emission line at 545 nm in the cases of all Tb(III) chelates), derivatives of certain transition metal chelates such as ruthenium(II) and osmium(II)-trisbipyridyl and trispyratsyl complexes (emission in the range of 550–650 nm).

A high electric field across the insulating films induces also to some extent solid state electroluminescence in the film. This solid state electroluminescence makes possible the excitation of luminophores also by energy transfer from the intrinsic emission centres, if the luminophores are located sufficiently close to the insulating film. This effect enhances the proximity effect required by homogeneous assays.

The insulating film-coated electrodes described in the present invention can be used in an EL cell which contains at least two electrodes: an insulating film-covered working electrode and a counter electrode.

The insulating film-coated working electrode should fulfill the criteria described above, and depending on the optical properties and the thickness of the conducting material it can be either optically transparent or non-transparent. Usually the transmittance of the sufficiently thin base conductor is high enough in the desired optical range. The use of a transparent working electrode makes possible the measurement of electrically excited luminescence through the working electrode.

The selection of the counter electrode of the method is not critical. Conventional inert electrode materials (Pt, Au) are well suited. Often, even certain metals which are anodically dissolved can be used, because the measurements usually are made in the time scale where the anodic products from counter or auxiliary electrode do not have time to diffuse to the working electrode. Also some metal oxide electrodes, such as indium tin oxide, are well suited as an anode material. In this case the anode material can be readily made optically transparent. Stainless steel is also advantageous electrode material. If a non-transparent metal electrode serves as a counter electrode its shape can be chosen so that the luminescence is measurable behind the counter electrode. For instance, a wire electrode covering only a very small part of the surface of the working electrode can be used or hole(s) drilled through the anode material allow the light detection behind the anode. Optically transparent counter electrode can be prepared from ad equate film, e.g., from plastic or glass coated with a thin Au-film which can be further coated with a thin shielding film allowing electron and/or hole tunnelling through the outer film.

If the thickness of the insulating film on the working electrode is suitable, the excitation of the label in the detection stage can be done by cathodic voltage pulse train, but in the case of base material being anodically oxidisable material such as Si, Al, Be or Mg, it is sometimes beneficial to grow the oxide film thicker by oxidising anodic pulse before each cathodic excitation pulse.

Depending on the sensitivity range needed for the analyte (s), either a low-cost semiconductor detector or more expensive and more sensitive photomultiplier tube are suitable light detectors for the electroluminometer.

The method of the present invention may be used to detect a molecule having the form $L_n$, -$X_x$-$Y_y$, where L is label or mixture of different kinds of labels, the label being a derivative of an organic luminophore, like a derivative of fluorescein, aminonaphthalenesulphonic acid, salicylates, rhodamines, or coumarines; a derivative of lanthanide chelates, like a derivative of Tb(III), Eu(III), Y(III), Sm(III), Dy(III), Gd(III) chelates; a derivative of transition metal chelates, like ruthenium(II)-trisbipyridyl- or ruthenium(II)-trispyrazyl chelates; where one or more of the derivatives are bound through suitable functional groups either directly or through one or more of linking compounds X to the compound Y, where Y is exemplified as protein, antibody, enzyme, or nucleic acid, which have affinity against the analyte to be quantified, and wherein the integral subscripts n, x, and y express the number of L, X, and Y, and are equal or larger than 1, and where compound Y can bind to a cell, a cell component, a virus, bacterium, nucleic acid, DNA, RNA, DNA-fragment, RNA-fragment, polysaccharide, protein, polypeptide, enzyme, metabolite, hormone, pharmacological substance, medical drug, alkaloid, steroid, vitamin, amino acid, carbohydrate, environmental pollutant, or antibody, and where the joint compound X may contain, as the essential linking function, a chemical group such as ureido, thioureido, amide, substituted imide, thioether, —S—S—, sulfonamide, or N-substituted sulfonamide, that is a part of a larger molecule or polymer attaching to the compound Y.

The method of the present invention includes a competitive bioaffinity method, where a competition of binding to Y on the surface of an insulating film-coated electrode is created between labelled analyte $L_n$-$X_x$-$A_a$ where the integral subscripts n, x and a express the number of L, X and A, and analyte A originated from the sample enabling the analyte concentration to be determined with insulating film-coated electrodes. Binding of $L_n$-$X_x$-$Y_y$ to A on the surface of the insulating film-coated electrode may inhibited by A originated from the sample.

The label L may be an enzyme capable of amplification of luminescent luminophores. For example, the enzyme may be alkaline phosphatase and the luminescent molecule may be a highly luminescent molecule or a lanthanide chelate generated by the enzyme.

The method of the present invention includes assays (i) in which only the label molecules located in the proximity of the insulating film-coated layer film can be excited by the electrical pulses enabling the analysis to be carried out by the homogeneous assay principle, and the separation of free label $L_n$-$X_x$-$Y_y$ is not required before the detection step, (ii) the quantitation is performed with heterogeneous principle and the free label $L_n$-$X_x$-$Y_y$ is removed from the proximity of electrode by a washing step before the detection step, and (iii) the basic immunoreaction is carried out in a separate incubation chamber with small-sized solid support materials, such as paramagnetic latex particles, whereby only the detection of the label is carried out on the electrode surface, after incubation and possible washings, by bringing the solid support materials into the proximity of the electrode.

The novel electrodes described in the present invention can be used to electric excitation of also other kind of luminophores than presented in Description and Examples of the present invention because it is obvious that also many other kind of molecules can be excited at insulating film-coated electrodes with the present methods. The use of insulating film-covered electrodes is not limited to certain equipment construction or just to analytical methods described hereby. In principle, also the reverse processes can be utilised as well. In this case, label molecules are illuminated with light and the resulting photocurrent induced by the photoinjection of carriers into probing electrode is measured or the potential of the probing electrode is measured allowing the quantitation of labels and analytes. In these applications, the probing electrode should preferably not be covered with an insulating film or favourably the thickness of the passive film should be less than 4 nm.

EXAMPLE 1

Preparation of insulator electrodes by anodising aluminium and modifying the surface by coating with polystyrene, and the immunoassay of phospholpase $A_2$ on the surface of these modified electrodes.

Anodic oxidation of Al-electrode. Al-electrode (Merck Art. 1057) moulded and cut to the final shape was first washed in ultrasound bath with hexane. Hexane was then allowed to evaporate. The electrodes were first oxidised galvanostatically with current density of 2 $mA/cm^2$ in 0.5 mol/L boric acid solution neutalised with ammonia until the anodising voltage of 2.92 V was reached. After this the anodising was continued potentiostatically until the current density was less than 10 $\mu A/cm^2$.

Coating oxidised electrode with polystyrene. The anodised parts of electrodes were coated first with polystyrene by sonicating the electrode for 10 s in the solution containing 0.7 mg/mL of polystyrene in benzene. Next the electrode was slowly lifted from the solution and allowed to dry at room temperature. The dry electrode was then slowly immersed into above-mentioned polystyrene solution further twice allowing the solvent totally to evaporate at room temperature between each immersion.

Coating electrode with antibody. Typically electrodes were coated with a monoclonal antibody by incubating the electrode overnight in TSA-buffer (0.05 mol/L Tris-HCl, pH 7.75, 0.9% NaCl, 0.05% $NaN_3$) containing the antibody (10 $\mu g/mL$; anti-$PLA_2$, clone 2E1, Labmaster Oy, Turku, Finland). Next day the electrode was washed six times with wash solution (0.01 mol/L Tris-HCl, pH 7.75, 0.9% NaCl and 0.02% Tween 20) and equilibrated overnight in saturation solution (TSA-buffer containing per liter 1 g bovine serum albumin 60 g sorbitol and 1 mmol $CaCl_2$). The equilibrated electrode can be dried at room temperature without washing and stored dry at least for 3 months.

Preparation of labelled antibody. The polyclonal sheep antibody specific to human pancreatic phospholipase $A_2$ (affinity purified by Labmaster Oy, Turku, Finland) was labelled with an isothiocyanate derivative of Tb(III)-1 chelate [$Tb^{3+}$-$N^1$-(p-isotiosyanatobenzyl)diethylene triame-$N^1$, $N^2$, $N^3$, tetra acetate], (Wallac Oy, Turku, Finland) by allowing the antibody to react with the chelate in the molar ratio of 1:60 at pH 9.5. The pH was adjusted with 1 mol/L $Na_2CO_3$ solution. The labelled antibody was separated from unreacted chelate by gel filtration (Sepharose 6B 1×50 cm, Sephadex G-50 1×5 cm) using TSA-buffer as eluent. Typically 5–10 chelate molecules can be bound in this way to one antibody molecule. To improve the stability, 0.1% bovine serum albumin was added to labelled antibody.

Preparation of standards. The standards of human $PLA_2$ (0, 1, 5, 9, 54, 324 ng/mL, Labmaster Oy, Turku, Finland) were prepared in TSA-buffer containing 7% bovine serum albumin.

Figure 4:
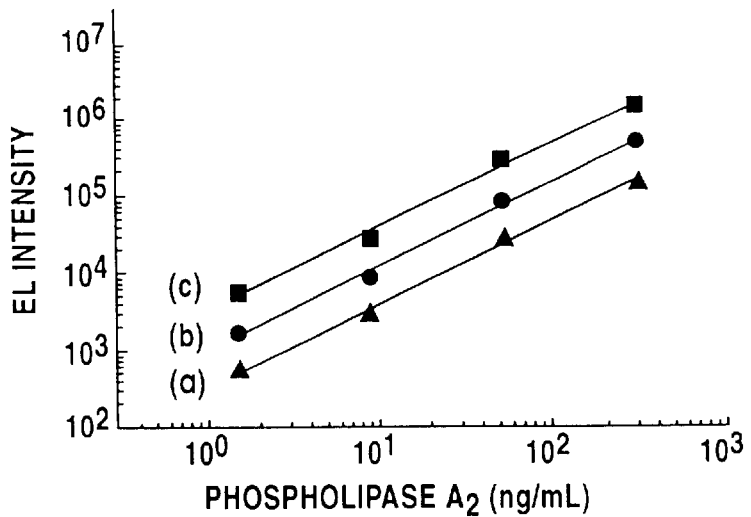
FIG. 4 illustrates standard curves of an immunometric assay of phospholipase $A_2$, in which the working electrodes are covered with (a) a natural oxide layer, (b) an anodized oxide layer, and (c) an anodized oxide layer covered with polystyrene.

Immunoassay. The immunoassay was carried out in the wells of microtiter strips. First, 25 $\mu L$ of standard and 175 $\mu L$ assay buffer (0.05 mol/L Tris-HCl, pH 7.75, 0.9% NaCl, 0.5% $NaN_3$, 0.5% bovine serum albumin, 0.05% bovine gammaglobulin and 0.01% Tween 40) were added. Next the electrode was added and after incubation for 1 h the electrode was washed with g wash solution and allowed to react with labelled antibody (500 ng/200 $\mu L$) for 1 h. After the reaction, the electrode was washed and the EL was measured in the measuring solution (0.2 mol/L borate buffer, pH adjusted to 7.75 with sulphuric acid) containing alternatively either 0.01 mol/L $NaN_3$ or 1 mmol/L $K_2S_2O_8$. FIG. 4 shows typical standard curves obtained in the assays, where (a) electrodes were air-oxidised, (b) electrodes were anodised with 2.92 V, and (c) electrodes anodised with 2.92 V and coated with thin polystyrene layer as described above (in the meaning solution of 1 mol/L $K_2S_2O_8$). The measurements were performed using aluminium cup electrodes and the instrument described in an academic dissertation of S. Kulmala (University of Turku, Tuku, Finland, 1995, pp. 34–35). In the measurement the excitation pulse was 200 ms and −10 V with the frequency of 100 Hz. The intensity of EL was integrated during 200 excitation pulses.

EXAMPLE 2

Modifying surface of an insulator electrode by coating with epoxy resin and immunoassay of TSH on the surface of these modified electrodes.

The electrodes were cleaned and anodised as described in Example 1 and the electrodes were covered with thin layer of epoxy resin.

Coating electrodes with epoxy resin. Both components of the Super epoxy glue (Loctite Finland Oy, art. n:o 120-1, Finland) were dissolved 1% (w/v) in toluene. The components were mixed 1:1 and the electrode was immersed into this solution in ultrasound bath and then lifted slowly out of this solution. The flowing solution from the lower edge was dried and the electrode was allowed to dry at room temperature until toluene was evaporated and then further in an oven at 40° C. for 24 h. Thicker coatings can be made by repeating the procedure.

Coating electrode with antibody. Electrodes were coated with antibody by physical adsorption by incubating the electrode in TSA-buffer containing the coating antibody (clone 8661, specific to the alpha chain of TSH, Pharmacia, Uppsala, Sweden) 30 $\mu g/mL$ for 3.0 h. After the coating the surface was washed with running wash solution and equilibrated overnight in TSA-buffer, pH 7.75, containing 0.1% bovine serum albumin and 5% D-sorbitol. After the equilibration the electrodes were dried and they were stable in storage for at least one year.

Preparation of labelled antibody. The labelled antibody for the assay of TSH was prepared in the same way as in Example 1. In this case the monoclonal antibody that is specific to the β-chain of TSH (clone 5404, Medix Oy, Helsinki, Finland) was labelled.

Preparation of standards. TSH standards (0, 0.25, 1.5, 9, 54, 324 $\mu U/mL$) were prepared by diluting the stock standard (Scripps Laboratories Inc, San Diego, USA) in TSA-buffer containing 7% bovine serum albumin.

Figure 5:
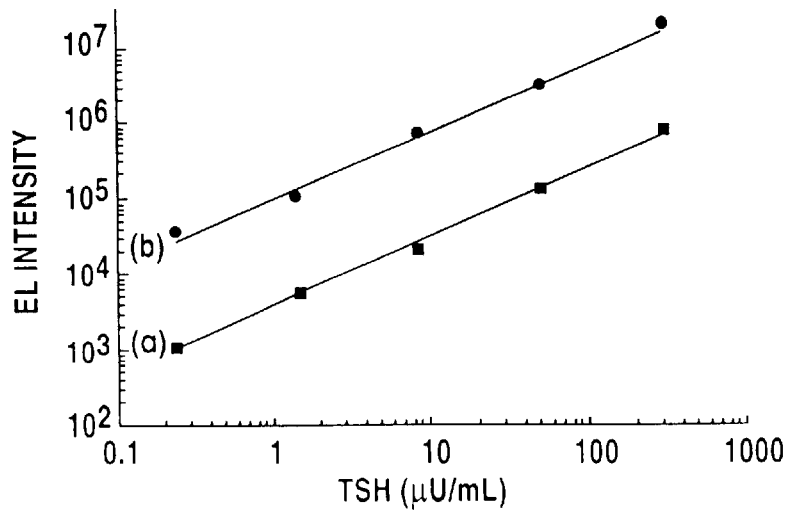
FIG. 5 depicts standard curves of an immunometric assay of TSH in which the working electrodes are aluminum electrodes covered with (a) natural oxide layer, (b) a layer modified by anodization and by coating with an epoxy plastic layer.

Immunoassay. TSH standard (20 $\mu L$) and 180 $\mu l$ (300 ng) of labelled antibody were added to the polystyrene wells. After incubation for 1 h, the electrode was washed and the EL was measured as in Example 1a–1b, but using the electroluminometer constructed by modifying an Arcus fluorometer (Wallac, Turku, Finland) The rake electrodes were as in FIG. 3*c*. FIG. 5 displays steward curves obtained with electrodes covered (a) with naturally exiting oxide film, and (b) with electrodes covered with an anodic oxide film and an epoxy film.

EXAMPLE 3

Competitive immunoassay of thyroxine (T4) whereby the insulator electrodes were anodised aluminium electrodes covered with polystyrene.

Labelling of thyroxine. Thyroxine was bound to gelatine as follows. T4-N-hydroxysuccinimide ester (1 mg, Wallac Oy, Turku, Finland) was dissolved in 194 mL of dioxane and 0.1 mL of this solution was added to 1 mL of 0.05 mol/L phosphate buffer, pH 7.3, containing 20 mg of gelatin (E. Merck, Darmstadt, Germany). After the reaction overnight at +4° C. gelatin was separated from small-molecular reagents by gel filtration using PD10-column (Pharmacia, Uppsala, Sweden) and phosphate buffer as eluent as above. The purified conjugate was labelled with isothiocyanate derivative of terbium chelate as in Example 1, but in this case the molar ratio of Tb-chelate to gelatin was 200:1. By assumption that the molecular weight of gelatin is 1 million it is possible to bind about 100 Tb-chelates to one gelatin molecule.

Coating electrode with antibody. Electrodes were coated with rabbit anti-mouse immunoglobulin (Dako, Glostrup, Denmark) by incubating the electrode overnight in 0.1 mol/L phosphate buffer, pH 4.9, containing the antibody 5 µg/mL. Next day the electrode was washed with wash solution as in Example 1 and equilibrated overnight in TSA-buffer containing 0.1% bovine, serum albumin, 6% D-sorbitol and 1 mmol/L $CaCl_2$ The coated electrode was dried without washing. It could be stored at room temperature without loss of activity for at least 3 months.

Preparation of standards. The standard of T4 (0, 10, 50, 100, 150 and 300 nmol/L) were prepared in 0.01 mol/L HEPES-, 0.001 mol/L sodium phosphate buffer, pH 7.4, containing 0.1 mol/L NaCl and 0.1% $NaN_3$ (HEPES-buffer), and 0.1% casein.

Figure 6:
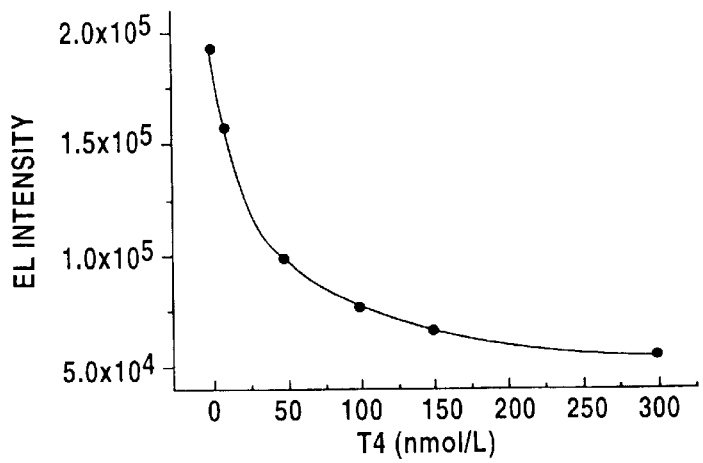
FIG. 6 shows a standard curve of a competitive assay of thyroxine (T4) in which the insulating film-coated electrodes were anodized aluminum electrodes.

Immunoassay. To the wells of microtiter plates 20 µL of standard were pipetted with 100 µL (0.5 ng) monoclonal mouse anti-T4 antibody (Medix Inc, USA) and 100 µL of gelatin-T4-Tb-conjugate (100 ng/mL). The electrode was added to the well and after incubation for 1 h the electrode was washed 5 times and the measurement was done as in Example 2. The standard curve is shown in FIG. 6.

EXAMPLE 4

Detection of Philadelphia chromosome by DANA hybridisation method whereby the insulator electrodes were made of anodised aluminium and coated with polystyrene.

Labelling the probe with Tb-chelate. The oligonucleotide containing amino groups (TTCGGGAAGTCGCCGGTCAT CGTAGA-(C-$NH_2$)$_{25}$-5', Wallac, Turku Finland) was labelled with Tb-chelate as in Example 2 except that the labelled nuclectide was purified using NAP-5 and NAP-10 columns (Pharmacia, Uppsala, Sweden).

Labelling the probe with biotin. For the assay, also another probe (C-(NH2-C)-GTCGTAAGGCGACTG GTAGTTATTCCTT-5', Wallac, Turku, Finland) was prepared. The N-hydroxysuccimide derivative of biotin was allowed to react in 3.7 µL of N,N-dimethyl formamide overnight with the probe (5 nmol in 50 µL, in molar ratio of 50:1) at pH 9.5, at +4° C. pH was adjusted by adding $Na_2CO_3$ so much that the fine molarity was 50 mmol/L. The probe was purified as the one labelled with Tb-chelate.

Coating electrode with streptavidin. The electrode was coated by incubating for 12–15 h in TSA-buffer containing streptavidin 10 µg/mL. Next day the electrode was washed with wash solution and equilibrated overnight in TSA-buffer containing 0.1% $NaN_3$, 0.5% bovine serum albumin and 6% sorbitol overnight. The electrode was dried and stored dry.

Figure 7:
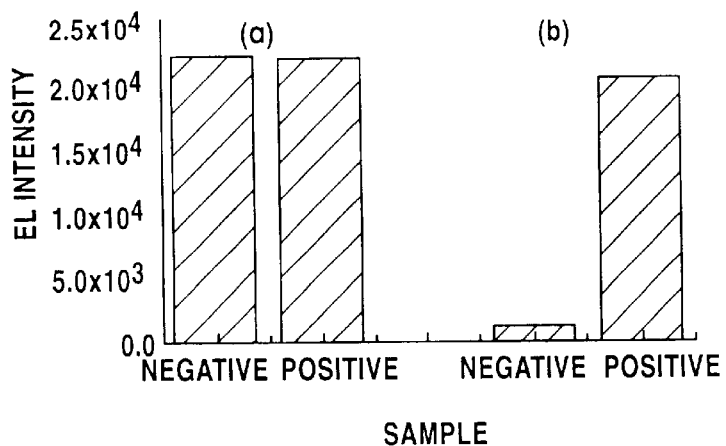
FIG. 7 illustrates the detection of Philadelphia chromosome by a DNA hybridization method in which the insulating film-coated electrodes were aluminum electrodes coated with polystyrene.

Hybridisation. A sequence of 170 base pairs, from K562 human cell line, amplified with PCR from chromosome $Ph^1$ (TYKS, Turku, Finland) was used as a positive sample and distilled water was a negative control. The positive sample and the negative control were kept in 100° C. for 10 minutes and then cooled down on an ice bath after which they were centrifuged with a microcentrifuge for 1 minute at 12000 rpm. Sample (50 µl) was pipetted into a disposable cuvette followed by 200 µl of the assay buffer, which contained 2 ng of biotinylated probe and 2 ng of the probe labelled with Tb(III) chelate. One liter of assay buffer (25 mM TRIS-HCl, pH 7.75) conned 33.72 g of NaCl, 0.25 g of $NaN_3$, 2.5 g of the bovine serum albumin, 0.25 g bovine serum gammaglobulin, and 0.05 mL Tween 40. The reaction was allowed to proceed for 2 hours at 50° C. After the electrode was washed 6 times, EL was measured as in Example 2. FIG. 7 shows the results achieved with electrodes uncoated (a) and coated with polystyrene (b).

EXAMPLE 5

Modifying the surface of aluminium electrodes by silanisation and the immunometric assay of TSH on the surface of these modified electrodes.

Silanisation of the aluminium electrode. The oxide-covered aluminium electrode was first washed with toluene in ultrasonic bath and then dried at 100° C. for 1 hour Silanisation was carried out by sonicating the electrode twice for 30 seconds in a 5-% toluene solution of diclorom-ethylsilane. After the silanisation the electrode was rinsed once with toluene and twice with methanol.

Coating electrode with antibody. The electrode was coated as in Example 2.

Preparation of labelled antibody Anti-TSH antibody was labelled with the isothiocyanate derivative of Tb(III)-2-chelate as shown in Examples 1 and 2.

Preparation of standards. TSH standards were prepared as in Example 2.

Figure 8:
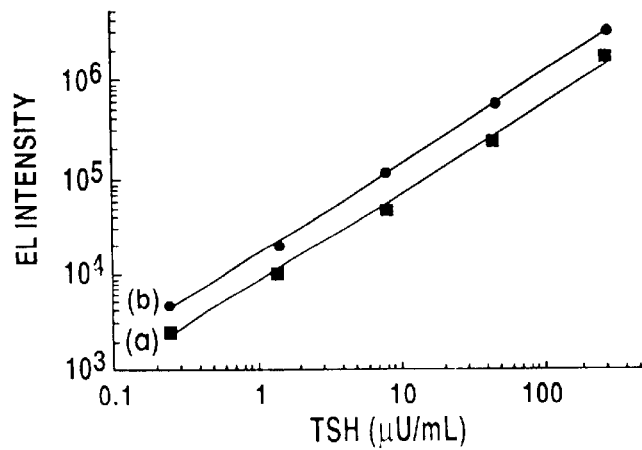
FIG. 8 depicts standard curves of an immunometric assay of TSH in which the electrodes were of oxide-coated aluminum (a), and (b) the surface of the oxide was modified by silanization.

Immunochemical determination. The immuochemical determination and measuring of the EL were cared out as in Example 2. The standard curves achieved in the tests are shown in FIG. 8.

EXAMPLE 6

Immunochemical determination of C-reactive protein by magnesium electrodes modified by coating the magnesium oxide surface of the electrode with polystyrene.

Coating electrode with polystyrene. A suitably sized Mg electrode (Merck Art. 5812) was washed in hexane using ultrasonic bath. Hexane was allowed to evaporate and the electrode was coated with polystyrene as in Example 1.

Coating electrode with antibody. The electrode was antibody-coated with mouse anti-human CRP antibody (clone 7H4, Labmaster Ltd., Turku) by incubating it for 1 hour in TSA buffer (pH 8.7) containing 10 µg/mL of antibody. The electrode was washed, stabilised and stored as in Example 1.

Preparation of labelled antibody. The antibody (House anti-human C-reactive protein, CRP, clone 5F3, Labmaster Ltd., Turku) was labelled as in Example 1.

Preparation of standards. Standards (0, 5, 50, 500, 2000 and 5000 ng/mL) were made by dissolving stock solution of CRP (Labmaster Ltd., Turku) in TSA buffer containing 7% bovine serum albumin and 1 mmol/L of $CaCl_2$ (the standard buffer).

Figure 9:
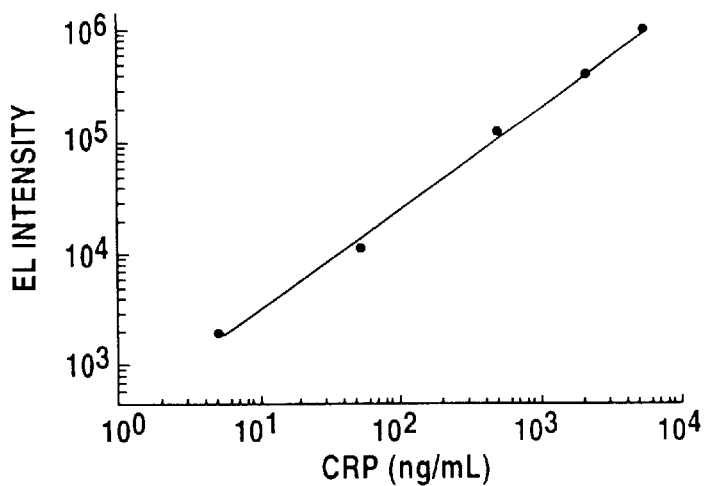
FIG. 9 shows a standard curve of an immunometric assay of CRP in which the insulating film-coated electrodes were oxide-covered magnesium electrodes coated with polystyrene.

Immunochemical detection. 10 μL of standard and 200 μL of standard buffer were added into a disposable cuvette (Brad, Cat Number 7590 15, Wertheim, Germany) the volume of which was reduced to 250 μL with a piece of Teflon. The coated electrode was inserted into the solution and incubated for 1 h. After washing (6 times) the labelled antibody in the standard buffer (200 μL, 500 ng) was added into the cuvette and incubated again for 1 h. After the incubation the electrode was washed and the EL was measured in the same way as in Example 1, except that the EL mu g itself that was done using a side-on type photomultiplier tube and a disposable spectophotometer cuvette made from polystyrene. The cuvette had Teflon holder for the plate working electrode and for Pt-wire counter electrode. The standard curve obtained is shown in FIG. 9.

EXAMPLE 7

Immunochemical determination of $\beta_2$-microglobutin on the surface of pulse-anodised silicon electrodes.

Silicon electrodes were made from n-Si discs doped with antimony, The orientation of Si discs was (III) and resistivity 0.008–0.015 Ωcm (Okmetic Ltd., Finland). The electrodes were cut into the size of 8.0×55 mm before surface treatments.

Anodisation of silicon electrode. Si electrode was anodised in a similar electrolyte solution as aluminium in Example 1, but using pulse anodising with a pulse train instead of DC anodising. The pulse train consisted anodic and cathodic pulses (200-μs each, +5 V or −5 V, frequency 100 Hz) with 10-ms intermittent zero level between the pulses, After anodisng, the electrode was rinsed with quartz distilled water.

Coating electrode with antibody. Typically oxide-covered silicon electrode (0.80×0.005×5.0 cm) was coated with mouse anti-$\beta_2$-microglobulin antibody (clone 6G12, Labmaster Ltd., Turku) by incubating overnight in 0.2 M $NaH_2PO_4$ solution, which contained 10 μg/mL of antibody. The next day the electrode %,as washed six ties with washing solution (0.01 M TRIS-HCl buffer, pH 7.75, 0.9% NaCl and 0.02% Tween 20) and saturated overnight in a saturation solution, which was 0.05 M TRIS-HCl buffer, pH 7.75, containing 1 g of bovine serum albumin, 60 g of sorbitol and 1 mmol $CaCl_2$ per liter. The saturated electrode can be stored dry at least for 3 months after washing (6 times).

Preparation of labelled antibody. Second monoclonal anti-$\beta_2$-microgiobulin antibody (clone 1F10, Labmaster Ltd., Turku) was labelled with isothiosyanato derivative of the $Tb(II)-4[Tb^{3+}-N-(4-isothiocyanatobenzoyl)$-diethylentriamine-$N^1, N^1, N^3, N^3$-tetra-acetate](Wallac Ltd., Turku) by allowing the antibody to react with the chelate in molar ratio of 1:60 at pH 9.5. pH was adjusted with 1 M $Na_2CO_3$ solution Labelled antibody was purified from unreacted chelate by gelfiltration (Sepharose 6B 1×50 cm, Sephadex G-50 1×5 cm) using TSA buffer (0.05 mol/L TRIS-HCl, pH 7.75, 0.9% NaCl, 0.05% $NaN_3$) as mobile phase. Typically in this way, 5–10 chelate molecule can be bound to one antibody molecule. To improve the stability, 0.1% of bovine serum albumin was added into the solution of labelled antibody.

$\beta_2$-Microgiobulin standards. Standards (0.4, 1.6, 4.0, 8.0 and 16 mg/L) were prepared from $\beta_2$-microgiobulin purified from human ascites fluid (75.5 mg/mL, Labmaster Ltd., Turku, Finland) into the TSA buffer. TSA buffer contained 7.5% bovine serum albumin.

Immunochemical determination. Immunochemical reaction was performed in disposable polystyrene cuvettes (1 mL, Brand, Cat. Number 7590 15, Wertheim Germany), the volume of which were reduced to 250 μl by a Teflon filler. Standards were diluted 1:50 with the assay buffer (0.05 mol/L TRIS-HCl, pH 7.75 containing 0.9% of NaCl, 0.05% of NaN3, 0.5% of bovine serum albumin and 0.01% Tween 20) and were added to the bottom of cuvette (40 μL). Then 160 μL of labelled antibody (500 ng containing 100 ng of labelled and 400 ng of unlabelled antibody, clone 1F10) in the assay buffer was added. Finally, the electrode coated with antibody was placed into the cuvette. Immunochemical reaction was allowed to take place for 1 h and the electrode was washed six times with washing solution.

Measuring of EL. EL was measured using electroluminometer and a cuvette especially prepared for this purpose. A Pt-wire served as counter electrode in the cuvette. Borate buffer, 0.2 mol/L, pH 7.75, containing 2 mmol/L $K_2S_2O_8$ was used as a measuring buffer.

Figure 10:
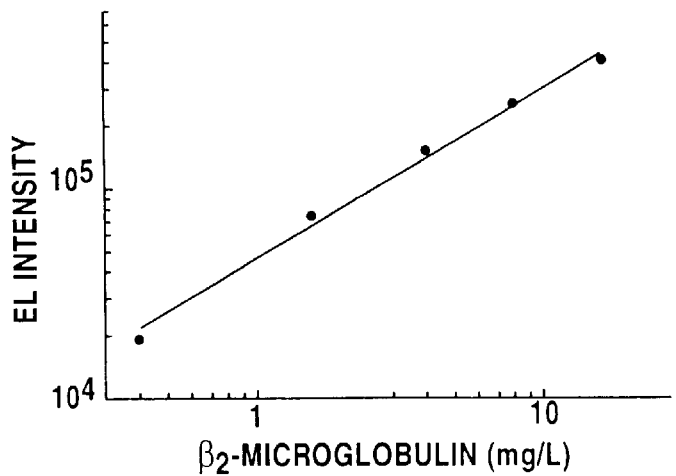
FIG. 10 illustrates a standard curve of an immunometric assay of $\beta_2$-microglobulin whereby the insulating film-coated electrodes were anodized silicon electrodes.

The standard curve obtained is shown in FIG. 10.

EXAMPLE 8

Immunometric detection of TSH using anodised silicon electrodes and anodised silicon electrodes which were additionally coated with polystyrene.

Coating electrodes with polystyrene. Silicon electrodes were prepared and anodised as in Example 7. The anodised electrodes were coated with polystyrene by sonicating the electrode for 30 seconds in a solution containing 1.5 mg/mL of polystyrene in benzene. After this, the electrode was lifted up slowly from the solution and allowed to dry at room temperature.

Figure 11:
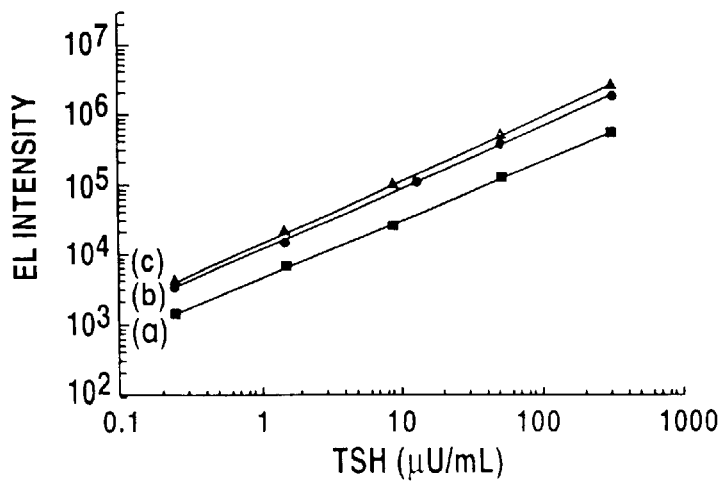
FIG. 11 depicts standard curves of an immunometric assay of TSH in which the working electrodes were (a) silicon electrodes covered with a natural oxide film, (by anodised silicon electrodes, and (c) anodized silicon electrodes covered with polystyrene.

Electrodes were coated with antibody as in Examples 2 and 7 (clone 8661 Phamacia, Uppsala, Sweden). The immunoassay was done in similar cuvettes as in Example 7, but using the labelled antibody prepared in Example 2 (80 ng of Tb(III)-2 labelled antibody/electrode) and the standard solution from Example 2. FIG. 11 shows the standard curves obtained with potentiostatic excitation (−10 V, 200 μs excitation pulses, 500 excitation cycles). Electrodes that were not anodised (a), anodised electrodes (by and the electrodes that were both anodised and coated with polystyrene (c).

EXAMPLE 9

DNA hybridisation method exploiting Si-electrodes modified by anodisation and coating with polystyrene.

Silicon electrodes were prepared from n-Si discs doped with antimony. The orientation of Si discs was (111) and resistivity 0.008–0.015 Ωcm (Okmetic Ltd., Finland). The electrodes were cut into the size of 8.0×55 mm before surface treatments. Anodisation of electrodes. Electrodes were anodised in a neutral 0.5 M ammoniumborate buffer first galvanostatically (1 mA/cm²) up to 5.2 V and then potentiostatically for 10 minutes.

Coating with polystyrene. The anodised parts of the electrode were coated with polystyrene at first by sonicating the electrode for 10 seconds in a solution containing 10 mg/mL of polystyrene in benzene. After is the electrode was lifted up slowly from the solution and allowed to dry at room temperature.

Figure 12:
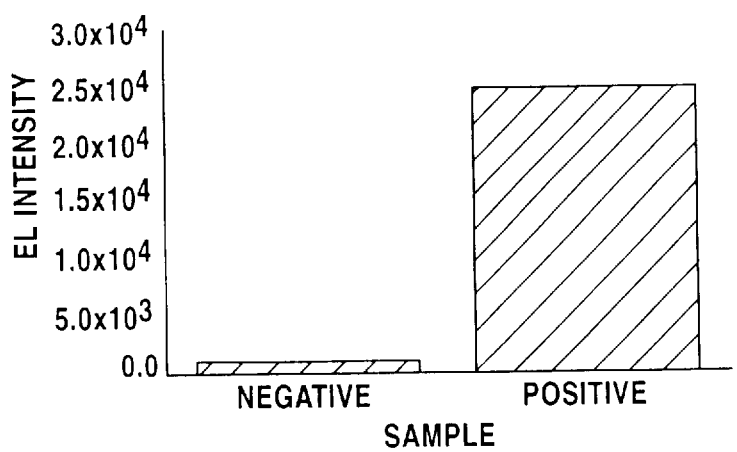
FIG. 12 shows the detection of Philadelphia chromosome by a DNA hybridization method in which the insulating film-coated electrodes were anodized silicon electrodes covered with polystyrene.

Hybridisation and the EL measuring were carried out as in Example 4 except that the electroluminometer and the cuvettes were as in Example 7. The results are shown in FIG. 12.

EXAMPLE 10

Immunochemical detection of T4 with anodised Si-electrodes.

The Si-electrodes were prepared and anodised as in Example 9 and coated with antibody as in Example 3.

Figure 13:
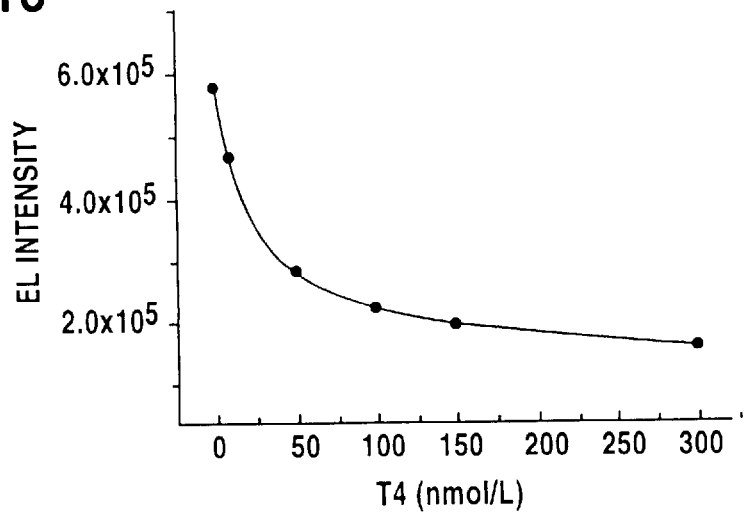
FIG. 13 illustrates a standard curve of a competitive assay of thyroxine (T4) in which the insulating film-coated electrodes were anodized silicon electrodes.

Immunochemical detection. Twenty µL of standard, 200 µL of monoclonal mouse anti-T4 antibody (Medix Biotech, Inc, USA) and 200 mL gelatin-T4-Tb-conjugate (50 ng/mL) were pipetted to a disposable cuvette. The electrode was placed into the cuvette and incubated for 1.5 h with shaking and then washed 6 times. The measuring was done in as in Example 7. The standard curve is shown in FIG. 13.

EXAMPLE 11

The immunochemical determination of TSH exploiting Zn-electrodes coated with alternating layers of polystyrene and paraffin.

Cup electrodes (volume 450 µl) made of Zn (Johnson Matthey Alfa Products) were first washed in an ultrasonic bath with hexane. Next, they were either treated cathodically in a peroxodisulfate solution in order to produce a thin oxide layer, or were coated directly with organic layers.

Cathodic oxidation of Zn-electrodes. The zinc cups were filled with 0.450 ml of 0.01 M $K_2S_2O_8$ solution in a 0.2 M borate buffer, pH 9.2, and catbodised with 10000 pulses (200-µs/pulse, amplitude of −10 V, and frequency of 100 Hz). After this, the electrodes were washed with quartz distilled water and allowed to dry.

Coating electrodes with organic layers. Oxidised or unoxidised electrodes were dipped slowly into a benzene solution of polystyrene (0.5 mg/mL). The electrodes were allowed to dry at room temperature for 24 h. Next, the electrodes coated with polystyrene were slowly dipped into a pentane solution of paraffin (1.0 mg/mL) and allowed to dry for 8 h. Then a new polystyrene layer was added as described in Example 8.

Figure 14:
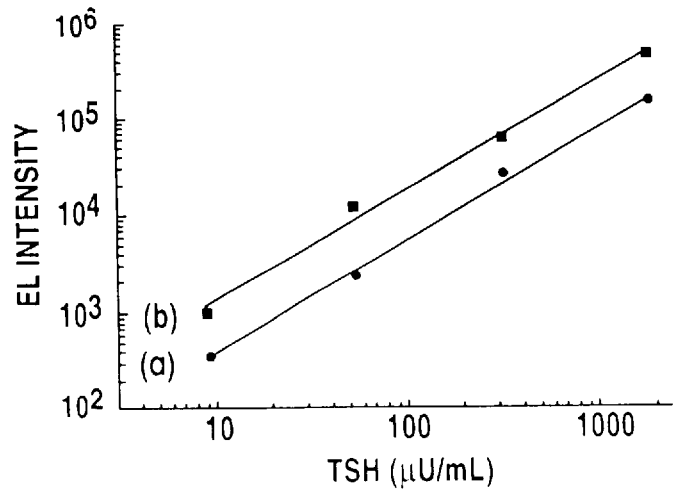
FIG. 14 depicts standard curves of an immunometric assay of TSH whereby the insulating film-coated electrodes were zinc electrodes either (a) first treated cathodically, or (b) directly coated with sequential layers of polystyrene and paraffin.

Immunoassay was done in the same way as in Example 1 but with the reagents from Example 2. Standard curves are shown in FIG. 14.

EXAMPLE 12

Immunometric determination of $\beta_2$-microglobulin exploiting insulator electrodes composed from glass plates covered with indium tin oxide surface film and coated with alternating layers of polystyrene and paraffin.

The electrodes (7.0×55 mm) were cut out from indium tin oxide-coated glass plates (Lohja Oy, Lohja, Finland) and then coated with polystyrene-paraffin-polystyrene layers as in Example 11.

Preparation of labelled antibody, Second monoclonal anti-$\beta_2$-microglobulin antibody (clone 1F10, Labmaster Ltd., Turku, Finland) was labelled with the isothiocyanato derivative of Tb(III)-2 chelate. The labelling was done as in Example 7 with the isothiocyanato derivative of Tb(III)-4 chelate. The label was purified by gelfiltration as in Example 7.

Figure 15:
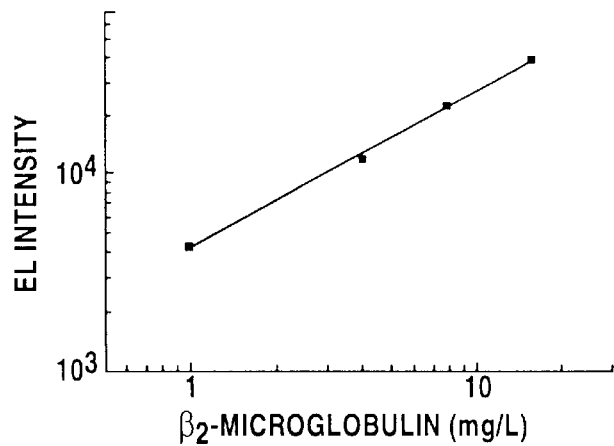
FIG. 15 shows a standard curve of an imrnunometric assay of $\beta_2$-microglobulin when the insulating film-coated electrodes were ITO-glass plates coated sequentially with polystyrene and paraffin.

Immunochemical determination and EL measurements were carried out as in Example 7. Standard curve is shown in FIG. 15.

EXAMPLE 13

Immunometric determination of $\beta_2$-microglobulin exploiting polyethylene terephtalate sheets covered with transparent gold film (Au-PET foils) and coated with alternating layers of polystyrene and paraffin.

Figure 16:
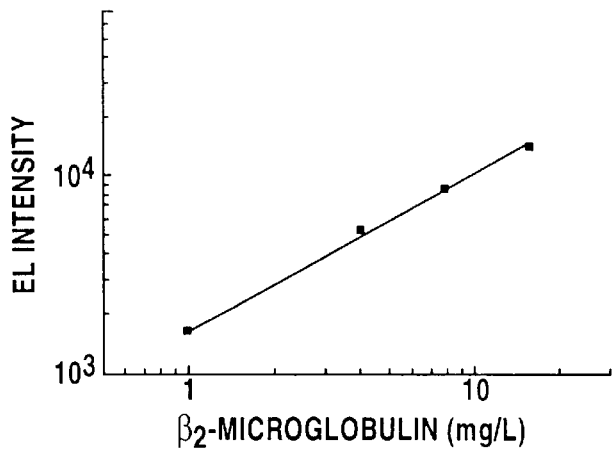
FIG. 16 illustrates a standard curve of an immunometric assay of $\beta_2$-microglobulin whereby the insulating film-coated electrodes were Au-PET films coated sequentially with polystyrene and paraffin.

Au-PET foils (Intrex film, type 28FX43, Sierracin, Sylmar, Calif., USA) were glued on glass plates (8.0×55 mm) and the plate electrodes obtained were coated with polystyrene-paraffin-polystyrene layers as in Example 7. The immunochemical detection of $\beta_2$-microglobulin was done as in Example 7, but using the labelled antibody prepared in Example 12. Standard curve is shown in FIG. 16.

EXAMPLE 14

Immunometric determination of CRP using insulator electrodes based on a conducting polymer film coated with alternating layers of paraffin and polystyrene.

Preparation of conducting polymer layer and coating it with insulating layers. Steel electrodes were coated with polyaniline according to the paper: J. Michaelson, A. McEvoy and N. Kuramoto, *React. Polym.* 17 (1992) 197. Electrodes coated with conducting polymer were coated further with paraffin layer by dipping then into a hexane solution containing 1.0 mg/mL of paraffin. The electrodes were allowed to dry for 12 hours. After this the electrodes were coated with polystyrene layer by dipping them into a benzene solution containing 1.0 mg/mL of polystyrene.

Figure 17:
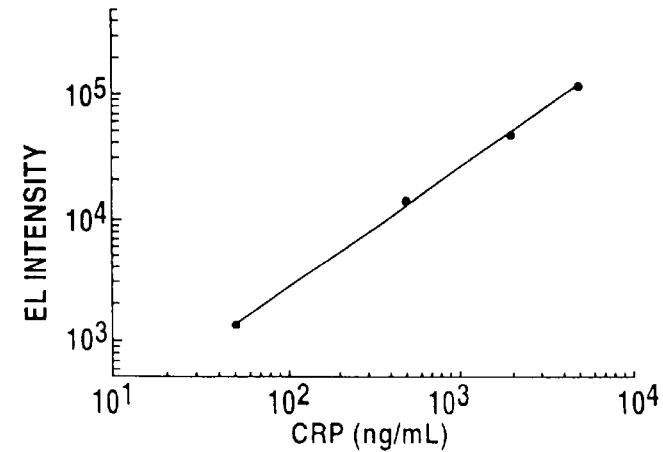
FIG. 17 depicts a standard curve of an immunometric assay of CRP whereby the insulating film-coated electrodes were polyaniline films coated sequentially with polystyrene and paraffin.

The coating of the electrodes with antibody and immunoassays of CRP were carried out as in Example 6. The resulting standard curve is shown in FIG. 17.

EXAMPLE 15

Immunometric determination of CRP exploiting insulator steel electrodes coated with aluminium oxide and polystyrene.

Coating steel with Aluminium oxide. Aluminium oxide layer was grown from $Al(CH_3)_3$ and water on the steel plate (50×50 mm) at 200° C. by using ALE-technique. Ninety cycles that produce about 5 nm thick oxide layer, were used in growing. Before the steel plate was taken out of the reactor, it was allowed to cool down to 60° C. in 10 mbar nitrogen atmosphere.

Aluminium oxide-coated steel was cut to 7.0 mm wide strips and they were covered with a thin polystyrene layer by dipping them twice into a benzene solution containing 0.7 mg/mL of polystyrene. The strips were allowed to dry between and after dipping for 8 h at room temperature.

Figure 18:
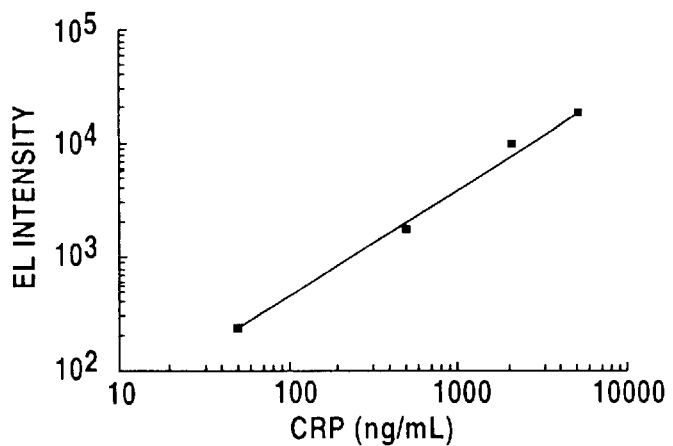
FIG. 18 shows a standard curve of an immunometric assay of CRP whereby the insulating film-coated electrodes were of steel coated with aluminium oxide and polystyrene.

Immunoassay was done in the same way as in Example, except that TSA buffer (pH 7.8) were the incubation buffer. Standard curve is shown in FIG. 18.

EXAMPLE 16

Detection of mouse IgG by labels emitting short- and long-lived emission exploiting oxide-covered magnesium coated with polystyrene.

Magnesium electrodes were coated with polystyrene as described in Example 6 and coated with mouse IgG as in Example 1.

Preparation of labelled antibodies. Rabbit antibody to mouse IgG (Dako, Denmark) was labelled with fluorescein-5-isothiocyanate (Sigma, F-7250) as the antibody was labelled with Tb(III)-1-isotiocyanate in Example 1. The molar ratio of antibody to label was 1:200. Accordingly, the same antibody was labelled with Eu(III)-3-isothiocyanate. The molar ratio of antibody to label was 1:100.

Figure 19:
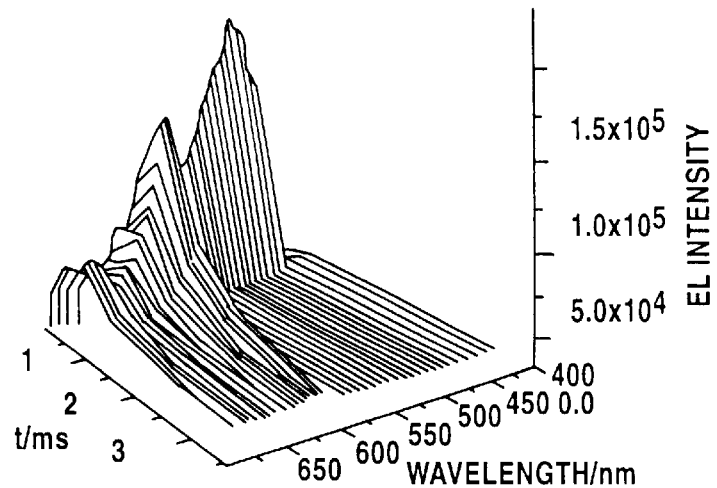
FIG. 19 illustrates a recorded EL spectra showing simultaneous excitability of a short-lived and long-lived EL-emitting labels.

Detection of mouse IgG. The immunreaction was made as in Example 6. Labelled antibodies were added in molar ratio of 1:01 (Eu(III)-3-label as an excess, total amount 200 ng/mL). After 30-min incubation, electrode was washed with distilled water and transferred to a cuvette of time-resolved spectrometer and the EL-spectra were recorded with time slices of 500 µs (FIG. 19). nm spectrum shows that simultaneous short-lived (fluorescein label) and long lived (Eu(III)-3-label) emission can be separated by time-resolved detection. When electrode was coated with rabbit IgG, spectra of neither one of the labels were obtained. The spectra were recorded as in Example 1, with a spectrometer described elsewhere (S. Pihlajamäki and J. Kankare, J. *Anal. Instrum.* 18 (1986)171.).

EXAMPLE 17

Simultaneous measurement of TSH and $PLA_2$ using anodised polystyrene-coated aluminium electrodes.

Labelling of antibodies. Monoclonal antibody specific to human TSH (clone 5404, Medix Oy, Helsinki) was labelled with aminohexylethylisoluminol (AHEI) by the method of Schroeder et al.(*Methods in Enzymology*, Vol 57, M. DeLuca (Ed,), Academic Press, N.Y., 1978).

Figure 20:
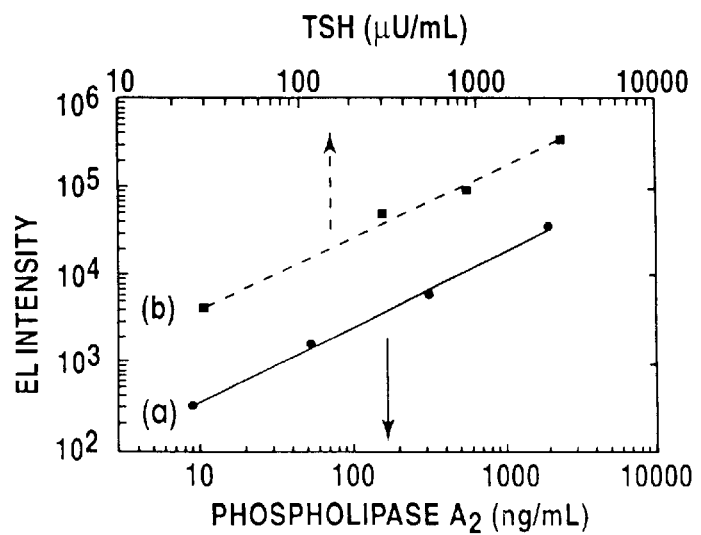
FIG. 20 depicts standard curves of simultaneous immunometric assays of TSH and $PLA_2$ whereby the insulating film-coated electrodes were anodized aluminum electrodes coated with polystyrene.

Immunoassay. $PLA_2$ and TSH standards (25 µL of each) and 175 µL of mixture of antibodies in TSA-buffer (500 ng anti-$PLA_2$-antibody and 300 ng and-TSH antibody) were added into the cuvettes. Electrodes (7.0 mm×0.3 mm×50 mm) were inserted into cuvettes and incubated for 1 h with shaking. Electrodes were washed with a wash solution and EL was measured with an electroluminometer as in Example 16. Standard curves art shown in FIG. 20.

EXAMPLE 18

Immunoassay of $PLA_2$ using latex particles as the solid phase carriers and polystyrene-coated anodised aluminium cups.

Aluminium electrodes were anodised and coated with polystyrene as in Example 1.

Coating of latex particles with antibodies. Stock suspension of latex particles (Sigma, LB-8) was diluted to 1:100 with TSA buffer. Into this dilution (100 µL), 100 µL of solution containing 5.7 mg/ml ant-$PLA_2$ antibody (clone 2E1, Labmaster Oy, Turku, Finland) in TSA buffer and the mixture was incubated overnight. Particles were separated by centrifugation and washed with the wash solution. After this the latex particles wet saturated with 0.1% bovine serum albumin solution as in Example 1. Tb(III)-1 chelate—antibody preparate was the same as in Example 1.

Figure 21:
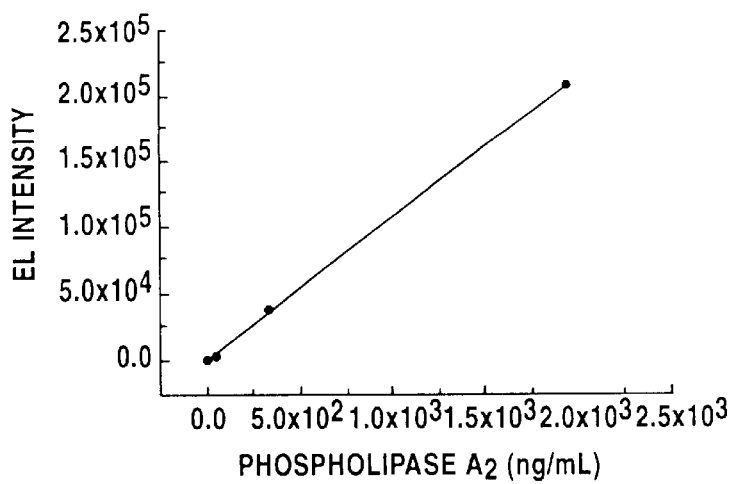
FIG. 21 shows a standard curve of an immunometric assay of phospholipase $A_2$ using latex beads whereby the insulating film-coated electrodes were anodized aluminum electrodes coated with polystyrene.

Immunoassay. About 180 million coated latex particles (20 µl of dilution of 1:20) were applied to 1.5-mL polypropylene centrifugal tubes saturated with bovine serum albumin. To this suspension, 20 µl of standard and 20 µl of Tb(III)-1-labelled antibody (500 ng) were added and incubated together for 20 min at room temperature. Then the particles were recovered by centrifugation and washed 2 times with the wash solution and once with EL-assay solution, to which 0.02% TWEEN 40 (w/v) were added. In the particles were suspended into EL measurement solution and EL was measured by using the cup electrodes. FIG. 21 shows the standard curve obtained.

EXAMPLE 19

Enzymatic amplification in an immunoassay of $PLA_2$ with latex particles as the solid carriers exploiting polystyrene-coated magnesium electrodes.

Magnesium electrodes were coated with polystyrene film as in Example 6. Latex particles were coated with antibodies as in Example 18.

Labelling of antibodies with alkaline phosphatase. Polyclonal sheep anti-$PLA_2$ was labelled with alkaline phosphatase (ALF) with maleimide (E. Ishikawa, M. Imagawa, S. Hashida, S. Yoshitake, Y. Hamuguchi and T. Ueno, *J. Immunoassay*, 4 (1983) 209.).

Figure 22:
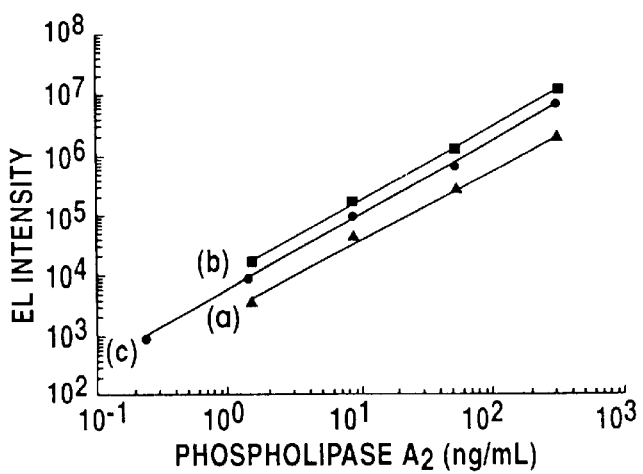
FIG. 22 illustrates standard curves of immunometric assays of phospholipase $A_2$ whereby enzymatic amplification was applied measuring directly 5-fluorosalicylic acid-label (a), and by producing ternary Tb(III) complex prior to EL measurements, applying total EL(b) or time-resolved EL detection (c) with polystyrene-coated magnesium electrodes.

Immunoasay. About 180 million coated latex particles (20 µl of dilution of 1:20) were applied to 1.5-mL polypropylene centrifugal tubes saturated with bovine serum albumin. To this suspension, 20 µL of standard and 20 µl of ALF-labelled antibody (600 ng) were added and the mixture was incubated for 15 min at room temperature. Then the particles were separated by centrifugation and washed 2 times with the wash solution. Particles were suspended into 200 µl of a solution containing 1 mmol/L substrate (phosphoric acid ester of 5-fluorosalisylic acid, FSAF, Kronern Systems Inc. Mississauga, Ontario Canada). The supernantant was separated after a 15-min incubation and 100 µL of it was transferred into EL-cuvette. It contained a disposable coated Mg-working electrode and 2 non-disposable platinum wires as the counter electrode. Then 150 µl of 0.1 M NaOH containing 1.0 mmol/L potassium peroxodisulfate were added. EL was measured though a 420-nm interference filter. The standard curve (a) is shown in FIG. 22. An alternative detection method was the following: 150 µL of supernatant was added to 100 µL of 0.5 mM Tb(III)-EDTA solution in 0.2 M NaOH. The solution was mixed with a pipette and allowed to react for 15 min. The solution was transferred to EL cuvette and 25 µL of 0.01 M potassium peroxodisulfate were added. After mixing with a pipette, EL-signal was measured. Standard curves are shown in FIG. 22. Both total (b) and time-resolved (c) signals (8 ms window and 50 µs delay) were measured through 545 nm interference filter by integrating over 10000 excitation pulses.

EXAMPLE 20

Immunoassay for $\beta_2$-microglobulin on microtiter strips by detaching Tb ions from antibodies after the immunoreaction and measuring free Tb ions with a new complex using anodised silcon electrodes.

Figure 23:
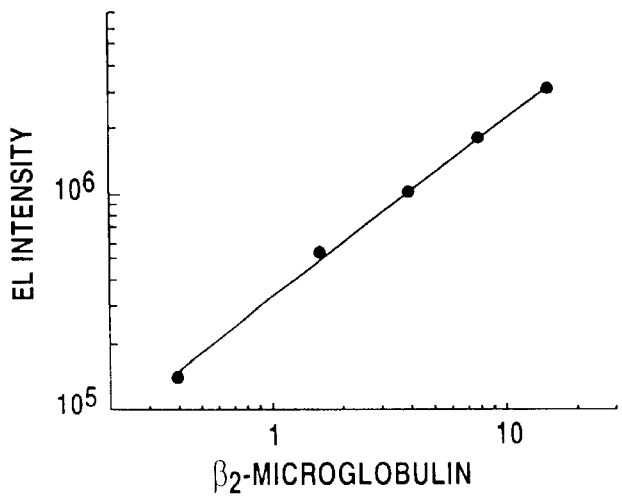
FIG. 23 depicts a standard curve of an immunometric assay of $\beta_2$-microglobulin whereby the insulating film-coated electrodes were made of anodized silicon.

The wells of microtiter strips were coated as described in Example 7 for the electrodes. The antibody was labelled with T(III)-1 chelate as in Example 7 and the immunoassay was performed also as in Example 7. After 1-h incubation, the wells were washed with the wash solution and 200 µL of 0.1 M glycine-$H_2SO_4$-buffer, pH 2.5, were added followed by a 15-min incubation. Then 150 µL of the incubated solution was taken into the cuvette and 45 µL of 0.5 mol/L $Na_2CO_3$ containing $5 \times 10^{-4}$ mol/L of ligand 5 was added The solution was mixed well and 205 µL of measuring buffer was adder The Tb(III)-5 chelate thus produced was quantified with oxide-coated silicon electrodes as in Example 7. The standard curve is shown in FIG. 23.

EXAMPLE 21

Immunoassy for $\beta_2$-microglobulin with liposomes as carriers of the label exploiting anodised silicon electrodes.

Figure 24:
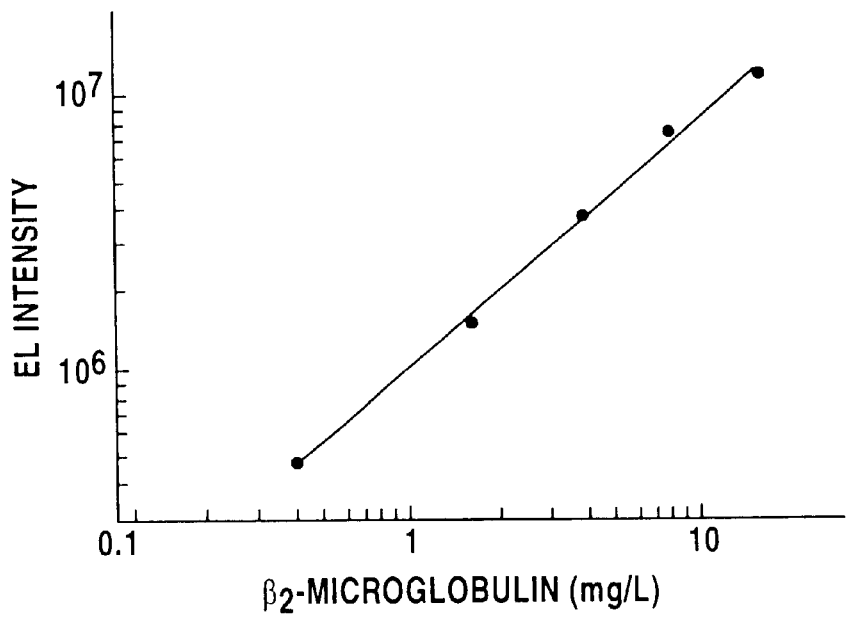
FIG. 24 shows a standard curve of an immunometric assay of $\beta_2$-microglobulin whereby the insulating film-coated electrodes were made of anodized silicon and the label was composed of liposomes containing luminophores.

Liposomes containing Tb-5-complex were prepared. They were bound to antibodies (anti-$\beta_2$-microglobulin, clone 6G12, Labmaster Oy, Turku, Finland) according to OP. Vonk, B. Wagner, Clin. Chem., 37 (1991) 1519. The immunoreaction was made as in Example 20, except that the buffer did not contain detergents. After washing, 230 µL of 0.1% Triton X-100, pH 3.2, in 0.1 M glycin buffer were added and incubated for 10 min. To this solution (200 µL), 60 µL of 0.5 mol/L $Na_2CO_3$ containing $5 \times 10^{-4}$ mol/L of ligand 5, were added Measuring buffer (240 µL) was added to the cuvette and EL was measured using 5 V (DC) anodised silicon electrodes as in Example 20. Standard curves are shown in FIG. 24.

EXAMPLE 22

Immunoassay for $\beta_2$-microglobulin employing UV-photochemical detaching of the label followed by measurement using anodised silicon electrodes.

Microtiter strips were coated as in Example 20.

Labelling of antibodies. The antibody (clone 1F10, Labmaster Oy, Turku, Finland) was labelled with a photodetachable label (Rhodamine Given sulfosuccinimidyl ester, Molecular Probes, R-7091, Eugene, USA) according to the manufacturer's instructions.

The immunoassay was carried out in the wells of microtiter plates as in Example 20, except that after the washing, 200 µL of 0.05 M $Na_2B_4O_7$ were pipetted into the wells.

Figure 25:
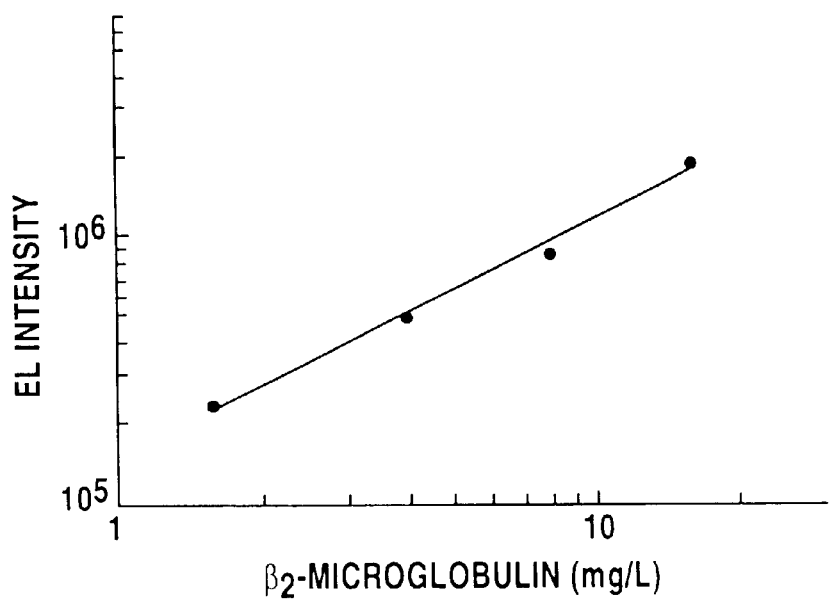
FIG. 25 illustrates a standard curve of an immunometric assay of $\beta_2$-microglobulin whereby the insulating film-coated electrodes were made of anodized silicon and the label was a luminophore that can be photodetached by UV-light.

Detaching the label with UV-radiation and EL-measurement. Microtiter strips were exposed to UV-light (Philips HPLR) for 4.0 min from the top. From each well, 180 µL of solution was taken and transferred to a cuvette and 320 µL of measuring solution were added. Total emission was measured as in Example 20 but with using a band-pass filter of 520 nm. Standard curve is shown in FIG. 25.

EXAMPLE 23

Homogeneous immunoassay for $\beta_2$-microglobulin exploiting energy transfer from donor to acceptor, enabling to observe delayed light emission from acceptor with an life-time related to the emission life-time of the donor.

Labelling of antibodies. Coating antibody (clone 6G12, Labmaster Oy, Turku, Finland) was labelled with Tb(III)-2-isothiocyanate as the Labelling of anti-TSH antibody in Example 2. Second monoclonal antibody (clone 1F10, Labmaster Oy, Turku, Finland) was labelled with Rhodamine B isothiocyanate (Sigma, R 1755) using label/antibody ratio of 90:1. Rhodamine B-labelled antibody was diluted after purification into an 0.2 M borate buffer, pH 7.8, including 4% bovine serum albumin.

Coating of electrodes. Silicon electrodes were coated with Tb(III)-2-labelled antibodies as were done in Example 7 with the non-labelled antibody.

Figure 26:
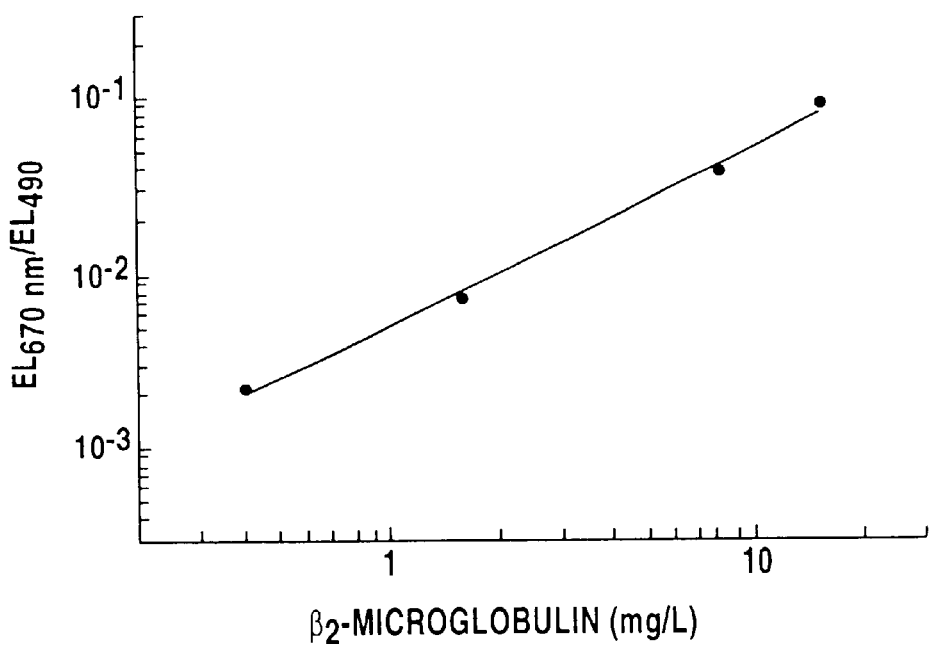
FIG. 26 depicts the standard curve of an immunometric assay of $\beta_2$-microglobulin based on energy transfer whereby the insulating film-coated electrodes were made of anodized silicon.

Immunoassay. Standard solution (40 µL; the same standards as in Example 7 in dilution of 1:50 made into 0.2 M borate buffer, pH 7.8, containing 4% of bovine serum albumin and 0.005% Tween 20) and 160 µL of Rhodamine B-labelled antibody (800 ng) were applied into the cuvette. Electrode was inserted into the cuvette containing disposable steel counter electrodes. After a 20-min incubation wit shaking, the cuvette was tightly closed and placed into the electroluminometer. The ratio of EL signal at 490 nm and 670 nm (delay time 500 µs; measuring window 3.0 ms) was measured. Results are in FIG. 26.

EXAMPLE 24

Homogeneous immunoassay for $\beta_2$-microglobulin using terbium(III)-chelate—containing latex particles and anodised silicon electrodes.

Preparation of latex particles and coating with antibodies. Into a saturated solution of Tb(III)-5 chelate in benzene, polystyrene was dissolved to obtain concentration of 20 mg/mL. This mixture (400 µL) was pipetted into 15 mL of pentane in an ultrasonic bath and sonicated for 5 min. Water (15 mL) was added and the mixture was shaken for 2 min. The latex parties were separated by centifugation and suspended in 0.5 mL of TSA buffer.

Labelling of antibodies. The coating antibody (clone 6G12, Labmaster Oy, Turku, Finland) was labelled with 9-fuorenylmethylclhoroformate (FMOC, Aldrich, No. 16,051-2) according the manufacturer's instructions with using label/antibody ratio of 80:1.

Coating of electrodes. Silicon electrodes we prepared and anodised as in Example 9. They were coated with FMOC-labelled antibody as was done with unlabelled antibody in Example 7.

Coating of latex particles. Latex particles were coated with antibodies (Clone 1F10, Labmaster Oy, Turku, Finland) as in Example 10.

Figure 27:
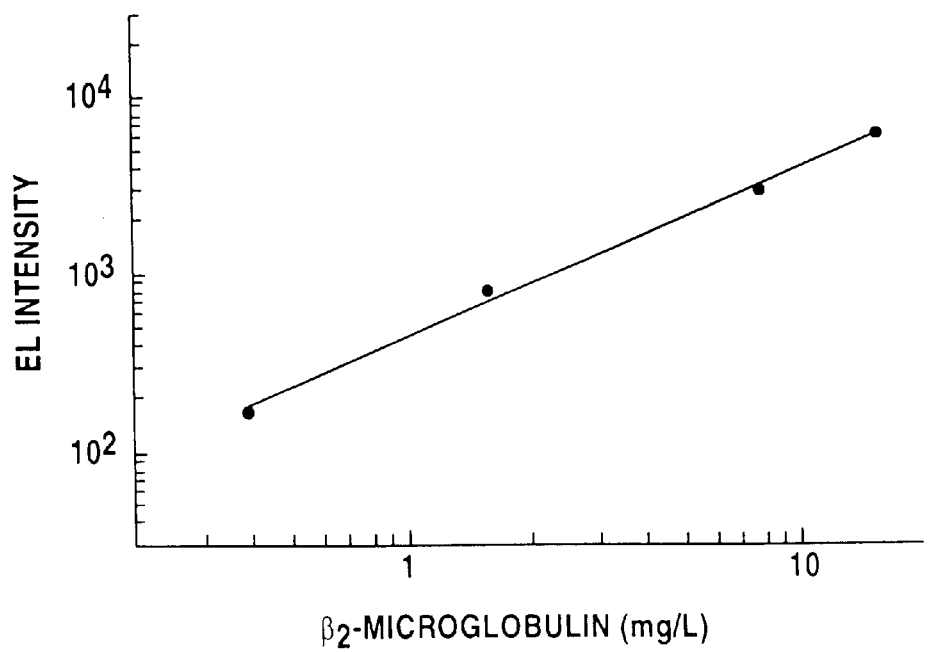
FIG. 27 shows a standard curve of an immunometric assay of $\beta_2$-microglobulin whereby the insulating film-coated electrodes were made of anodized silicon and the label was composed of polystyrene particles containing terbium chelates.

Immunoassy. Standard solution (40 µL; the same standard solutions as in Example 7 as a dilution of 1:50 made up by 0.2 M borate buffer, pH 7.8, including 4% bovine serum albumin and 0.005% Tween 20), 160 µL of the former buffer containing 1 mmol/L $K_2S_2O_8$ and 20 µL of the particle suspension were mixed in the cuvette. The reaction was allowed to proceed with shaking for 20 min and then 10 min without shaking. Eventually, EL was measured as in Example 7. Standard curve is shown in FIG. 27.

---

What is claimed is:

1. A method for electrical excitation of a label molecule, comprising
at least partially immersing an electrode in an electrolyte solution containing at least one label molecule;
exciting said label molecule by an electrical pulse from said electrode, thereby producing an excited label; and
detecting luminescence emitted by said excited label;
wherein said electrode comprises an electrically conductive material and at least the portion of said electrode which is immersed in said solution is substantially covered with an electrically insulating film comprising aluminum oxide having a band gap equal to or greater than 5 eV,
wherein said electrically insulating film is covered by a shielding layer comprising an organic polymeric material.

2. The method of claim 1, wherein the electrically conductive material of said electrode has a resistivity below 10 Ωcm.

3. The method of claim 2, wherein said electrically conductive material is a member selected from the group consisting of metal, a conductive polymer, and an electrically conductive doped semiconductive material.

4. The method of claim 3, wherein said electrically conductive material is silicon or composite silicon made to be conductive by doping with other materials.

5. The method of claim 1, wherein said electrode is sufficiently transparent at a wavelength range of emission of said label that luminescence can be measured through said electrode.

6. The method of claim 1, wherein said label is a part of a detectable molecule which conforms to the formula $L_n-X_x-Y_y$, wherein
L is said label;
X is a linking compound;
Y is a compound having affinity against the analyte to be quantified, and is a member selected from the group consisting of proteins, antibodies, enzymes and nucleic acids, and wherein the integral subscripts n, x, and y express the number of L, X, and Y, and are equal to or larger than 1.

7. The method of claim 6, wherein said compound Y is capable of binding to at least one member of the group consisting of a cell, a cell component, a virus, a bacterium, a nucleic acid, a DNA, a RNA, a DNA-fragment, a RNA-fragment, a polysaccharide, a protein, a polypeptide, an enzyme, a metabolite, a hormone, an alkaloid, a steroid, a vitamin, an amino acid, a carbohydrate and an antibody.

8. The method of claim 6, wherein X comprises a chemical linking functional group selected from the group consisting of ureido, thioureido, amide, substituted imide, thioether, —S—S—, sulfonamide and N-substituted sulfonamide, and wherein said chemical functional linking group is a part of a larger molecule or polymer attached to Y.

9. The method of claim 6, wherein said label is a derivative of a compound selected from the group consisting of an organic luminophore derivative, a derivative of a lanthanide chelate and a derivative of a transition metal chelate.

10. The method of claim 9, wherein said organic luminophore is selected from the group consisting of fluorescein, aminonaphthalenesulphonic acid, salicylates, rhodamines and coumarines.

11. The method of claim 9, wherein said lanthanide chelate is a member of the group consisting of Tb(III), Eu(III), Y(III), Sm(III), Dy(III) and Gd(III) chelates.

12. The method of claim 9, wherein said transition metal chelate derivative is a derivative of ruthenium(II)-trisbipyridyl or ruthenium(II)-trispyrazyl.

13. The method of claim 6, wherein said electrode further comprises a compound Y' bound directly or indirectly to a surface of said electrode, said compound Y' having a specific affinity to the same analyte as Y, and wherein an affinity reaction takes place on a surface of the insulating film before said detecting step.

14. The method of claim 6, wherein a competition of binding to Y on a surface of said electrically insulating film is created between a labeled analyte which conforms to the formula $L_n-X_x-A_a$ wherein
A is an analyte of interest, and
the integral subscripts n, x and a express the number of L, X and A.

15. The method of claim 14, wherein binding of $L_n-X_x-Y_y$ to A on a surface of said electrically insulating film is inhibited by A originating from a sample.

16. The method of claim 6, further comprising a washing step which removes free label $L_n-X_x-Y_y$ from the proximity of said electrode before said detecting step.

17. The method of claim 6, further comprising an incubation step in which said detectable molecule is bound to a solid support in the form of particles prior to being excited.

18. The method of claim 17, wherein a luminophore is detached from the detectable molecule bound to a solid support before quantification of the luminescence signal.

19. The method of claim 6, wherein said label L is an enzyme capable of amplification of luminescent luminophores.

20. The method of claim 19, wherein said enzyme is alkaline phosphatase, and the luminescent molecule is a lanthanide chelate generated by said enzyme.

21. The method of claim 1, wherein more than one kind of label is used simultaneously.

22. A method according to claim 1, further comprising adding at least one coreactant capable of transforming at least one primary reducing or oxidizing component generated by said electrode, such that said at least one primary or oxidizing component is transformed into a secondary oxidizing or reducing component more suitable for exciting said label.

23. The method of claim 22, wherein said coreactant is selected from the group consisting of peroxodisulfate, peroxodiphoshate and hydrogen peroxide.

24. An insulating film-coated electrode, comprising an electrically conductive material,
- an electrically insulating film comprising aluminum oxide covering substantially all of said electrically conductive material, said film having a band gap equal to or greater than 5 eV; and
- a compound bound directly or indirectly to a surface of said electrode, said compound is capable of binding to a member of the group consisting of a cell, a cell component, a virus, a bacterium, a nucleic acid, a DNA, a RNA, a DNA-fragment, a RNA-fragment, a polysaccharide, a protein, a polypeptide, an enzyme, a metabolite, a hormone, an alkaloid, a steroid, a vitamin, an amino acid, a carbohydrate and an antibody;
- wherein said electrically insulating film is covered by a shielding layer comprising an organic polymeric material.

25. The insulating film-coated electrode of claim 24, wherein said electrode is sufficiently transparent that luminescence can be measured through said electrode.

26. The insulating film-coated electrode of claim 24, wherein said electrically conductive material is silicon or composite silicon made to be conductive by doping with other materials.

27. The insulating film-coated electrode of claim 24, wherein said electrically insulating film covering said electrically conductive material has a band gap greater than 5 eV.

28. The insulating film-coated electrode of claim 24, wherein said electrically insulating film has an average thickness of from 2 to 5 nm.

* * * * *

UNITED STATES PATENT AND TRADEMARK OFFICE
CERTIFICATE OF CORRECTION

PATENT NO. : 6,645,776 B2
DATED : November 11, 2003
INVENTOR(S) : Sakari Kulmala et al.

It is certified that error appears in the above-identified patent and that said Letters Patent is hereby corrected as shown below:

Title page,
Item [56], References Cited, OTHER PUBLICATIONS, change "Y. Ono" to
-- S. Ono --.

Column 11,
Between line 4 and the heading "Example 1", insert the following text:

```
FIG. 1 presents the electrodes used in the present invention and
the measuring instrument for luminescence. The working electrode is
composed of a conducting base material (C) and of a thin insulating
film (I) on its surface. The insulating film can be composed of one
or several layers of same or different insulating material (I₁, I₂
. . . Iₙ). The working electrode can be optically transparent or
non-transparent. With transparent working electrodes, the
measurement of the light can be done trough the working electrode
by detector D₂. A two-electrode cell is usually sufficient, but
also a conventional three-electrode cell, which is composed of a
working electrode and an auxiliary and a reference electrode such
as Ag/AgCl-electrode can be used, as well. The working electrode
(or auxiliary electrode) can be chosen geometrically so that the
measurement of the light is occurring from the direction of the
counter electrode (detector D₁) irrespective the counter electrode
being optically transparent or non-transparent to the light
generated. When both the working and the counter electrodes are
sufficiently transparent, the dual labelling and the measurement of
the light at two different wavelengths (filters F₁ and F₂) can be
done very simply without expensive optics or a beam divider. The
light detectors D₁ and D₂ can be photomultiplier tubes, but also
other less sensitive detectors are useful, when the concentration
of the analytes is sufficiently high in the samples. The light
measuring device depending on the application is either one or
multichannel gated integrator, or a photon counter.
```

Figure 2:
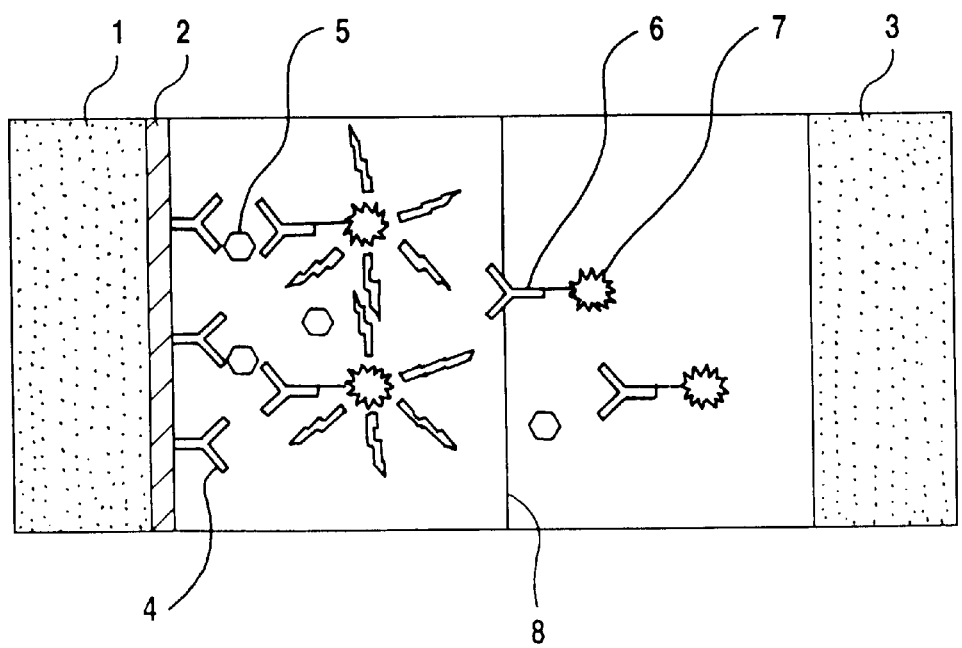
FIG. 2 depicts the measurement principle of an immunoassay of the present invention.

```
FIG. 2 presents the measuring principle of an immunochemical
reaction with insulator electrodes. The working electrode consists
of a base material C (1) and an insulating film I (2). Most
commonly, the immunoassay is performed using an immunometric
principle; then the insulting film I (2) is coated with antibodies
(4) which are specific to the analyte (5). The immunoassay is then
done so that the mixture of the sample and a label (7), i.e., a
labelled second antibody specific to analyte (5), is incubated in
the buffer solution in the contact with the surface of the working
electrode. This results in the formation of immunocomplexes
I-(4)-(5)-(6)-(7) on the surface of insulating film. If the
requirements of sensitivity for the determination of the analyte
```

UNITED STATES PATENT AND TRADEMARK OFFICE
CERTIFICATE OF CORRECTION

PATENT NO. : 6,645,776 B2
DATED : November 11, 2003
INVENTOR(S) : Sakari Kulmala et al.

It is certified that error appears in the above-identified patent and that said Letters Patent is hereby corrected as shown below:

Column 11 (cont'd), are not extremely high, the amount of the analyte can be quantified after this reaction step by exciting the label molecules (7), that are involved in the complex I-(4)-(5)-(6)-(7), by electric pulses. This so-called homogeneous assay principle is possible because the excitation of the label molecules is possible only to a certain distance (8) from the surface of the insulating film, whereas more distant label molecules are not excited. On the other hand, in the case of heterogeneous principle, the labelled antibodies not bound to complexes I-(4)-(5)-(6)-(7) [in other words the entities (6)-(7)] are washed away, providing a better sensitivity than the use of homogeneous assay principle. The chemical reactions occurring on the counter electrode (3) do not usually produce luminescence with the luminophores used in this invention.

Figure 3:
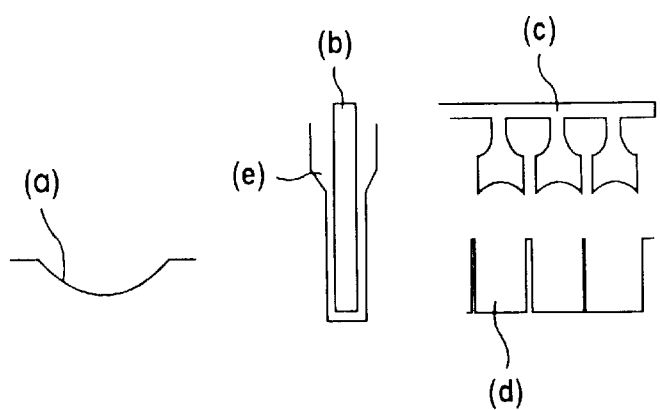
FIG. 3 shows various shapes of the insulating film-coated electrode of the present invention.

FIG. 3. Depending on the material of working electrodes (insulator electrodes) they can sometimes be moulded to a shape of a vessel or cup (a), in this case, the insulating film has to be prepared on the surface of the electrode only after accomplishing the shape of the electrode; all the insulator electrodes are generally applicable as plate electrodes (b), but metal-based insulator electrodes can be used in many different forms, e.g., as "rake electrodes" (c), used in some Examples.

Signed and Sealed this

Twenty-second Day of June, 2004

JON W. DUDAS
*Acting Director of the United States Patent and Trademark Office*